United States Patent [19]

Takaha et al.

[11] Patent Number: 5,827,697
[45] Date of Patent: Oct. 27, 1998

[54] PROCESS FOR PREPARING GLUCANS HAVING A CYCLIC STRUCTURE

[75] Inventors: Takeshi Takaha, Kobe; Michiyo Yanase, Hyogo-ken; Shigetaka Okada, Ikoma; Hiroki Takata, Kobe; Hiroyasu Nakamura; Kazutoshi Fujii, both of Amagasaki, all of Japan

[73] Assignee: Ezaki Glico Co., Ltd., Osaka, Japan

[21] Appl. No.: 560,739

[22] Filed: Nov. 20, 1995

Related U.S. Application Data

[62] Division of Ser. No. 415,152, Mar. 31, 1995, Pat. No. 5,686,132.

[51] Int. Cl.$^6$ ....................................... C12P 19/04
[52] U.S. Cl. ...................... 435/101; 536/1.11; 536/123.1; 536/123.12
[58] Field of Search ................................ 435/97, 99, 101

[56] References Cited

U.S. PATENT DOCUMENTS 5,364,936  11/1994  Oguma et al. ........................... 536/103

FOREIGN PATENT DOCUMENTS 6-62883  3/1994  Japan .

OTHER PUBLICATIONS

S. Kobayashi, "Fundamental Study and Application of Cyclodextrins," *Denpun Kagaku* 40(2):103–116 (1993).

Horikoshi et al., "Industrial Production of Cyclodextrins," I. Int. Symp. on Cyclodextrins, 25–39 (1981).

*Primary Examiner*—Elli Peselev
*Attorney, Agent, or Firm*—Dianne E. Reed; Bozicevic & Reed LLP

[57] ABSTRACT

The present invention provides glucans and derivatives thereof which are useful as raw materials in the starch processing industries, food and drink compositions, food additive compositions, and starch substitutes for biodegradable plastics, and processes for preparing the same. Particularly, it provides glucans and derivatives thereof having excellent properties such as higher solubility in water than conventional starches, lower viscosity and the glucans are not subject to retrogradation which is observed in conventional starches, and which are capable of preventing the retrogradation of starches.

8 Claims, 12 Drawing Sheets

(1) THE GLUCAN HAVING AN ACYCLIC STRUCTURE IN ADDITION TO A CYCLIC STRUCTURE
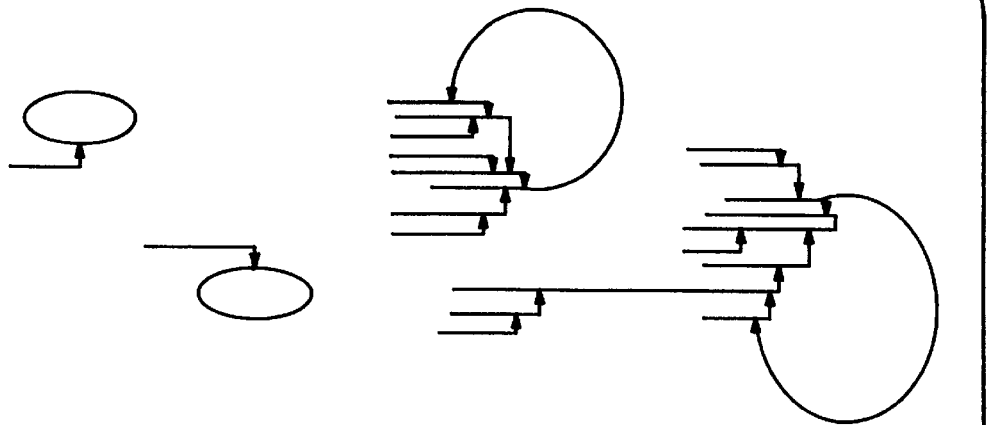
(2) THE GLUCAN HAVING ONLY A CYCLIC STRUCTURE COMPRISING ONLY ALPHA-1,4-GLUCOSIDIC BONDS
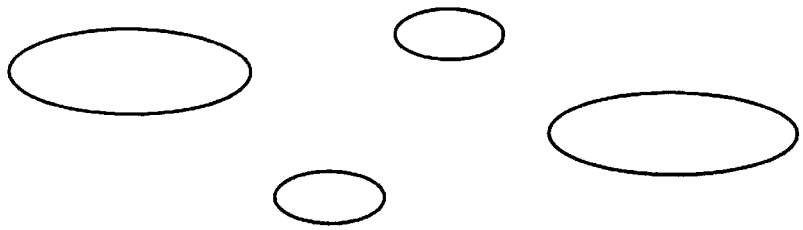
(3) THE GLUCAN HAVING ONLY A CYCLIC STRUCTURE COMPRISING ALPHA-1,4-GLUCOSIDIC BONDS AND AT LEAST ONE ALPHA-1,6-GLUCOSIDIC BOND
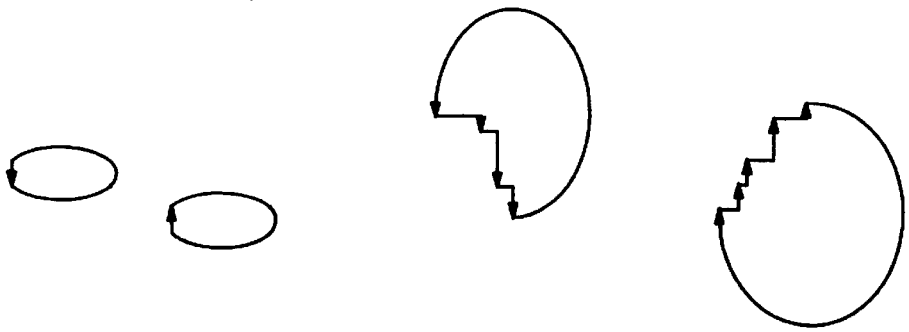
FIG. I

PROCESS FOR PREPARING GLUCANS HAVING A CYCLIC STRUCTURE

This application is a divisional of a U.S. application Ser. No. 08/415,152, filed Mar. 31, 1995, now U.S. Pat. No. 5,686,139.

BACKGROUND OF THE INVENTION

1. Field of the Invention

The present invention relates to glucans and derivatives thereof which are useful as raw materials in the starch processing industries, food and drink compositions, food additive compositions, infusion solutions, adhesive compositions, inclusion materials and adsorption materials. The glucans and derivatives thereof are also useful as anti-retrogradation agents for starch, and starch substitutes for biodegradable plastics. More particularly, the present invention relates to glucans having one cyclic structure comprising at least 14 alpha-1,4-glucosidic bonds, derivatives thereof, and processes for preparing the same.

2. Description of the Related Art

Starches are polymer materials which have been heretofore used as raw materials for the production of maltose, starch syrups, cyclodextrins, and the like, food and drink compositions, food additive compositions, and materials for biodegradable plastics.

However, conventional starches have problems such as lower solubility in water, solution instability, and high viscosity in solution when employed for the above-described uses. Starches generally have a low solubility in water. Therefore, it is necessary to conduct a heat treatment, or chemical treatment with organic solvents, acids, alkalis, etc., so as to dissolve the starches and thus improve solubility in water.

Dissolved or gelatinized starch is retrograded rapidly to form an insoluble precipitate. Such retrogradation of starch changes its properties, such as the viscoelasticity of the starch solution, the adhesiveness of the starch, and the like. Also, foods containing starch may encounter problems such as reduction of its water holding property, shape holding property, freezing resistance, digesting properties, and the like.

Moreover, gelatinized starch has a high viscosity due to the fact that the amylopectin in starch is an extremely long molecule in which a number of cluster structures are arranged. Since gelatinized starch has a high viscosity, there is a problem in that it is difficult to handle the starch in the case where starch is used as a raw material for the production of maltose, cyclodextrins, etc. For example, where gelatinized starch of a certain high concentration is transported through a pipe, the pipe may become clogged.

Thus, the above-described properties of conventional starches (low solubility, solution instability, and high viscosity in solution) have limited the utilization of starches in food and other applications.

Recently, research has been conducted to improve the solubility and retrograding properties of starches by reducing molecular weight using an enzyme treatment, chemical treatment, or physical treatment. These treatments have somewhat successfully solved the above-mentioned problems of starches. However, it is difficult to prevent excess reduction of the molecular weight of starches, and the starches losing their inherent properties. Also, as a result of these treatments, starches have increased reducing capacity. Therefore, when starches are heated with a protein, an amino acid, etc., they are subject to coloring due to the reaction with these materials. This also restricts their useful applications.

For example, one enzyme treatment, involves a method of using a so-called D-enzyme (disproportionating enzyme (EC 2.4. 1.25)) or amylomaltase (EC 2.4 1.25). The D-enzyme, which was initially discovered in potato, is known to exist in various plants, and microorganisms such as *E. coli*. The enzyme is designated as a D-enzyme when it is derived from plants, and as amylomaltase when it is derived from bacteria.

D-enzyme has been believed to catalyze the transglycosylation reaction (disproportionation reaction) of maltooligosaccharides. It catalyses the transfer of a glucosyl or maltooligosyl unit from the non-reducing end of a donor molecule to the non-reducing end of an acceptor molecule. Thus, the enzyme reaction results in the disproportionation of initially given maltooligosaccharides. It has been reported that this disproportionation reaction occurs when high molecular weight starch, such as solid starch or amylopectin, is used as a donor and glucose or maltooligosaccharide is used as an acceptor. However, D-enzyme has not been used to solve the above-described problems.

On the other hand, the use of a cyclic polysaccharide consisting of D-glucose, i.e., a cyclic glucan is considered to be a substitute for the above-described starches.

Cyclodextrins, which are glucans having only a cyclic structure comprising an alpha-1,4-glucosidic bond, have been know as conventional cyclic glucans. These cyclodextrins, which are synthesized by cyclodextrin glucanotransferase (CGTase) on starch, typically have a degree of polymerization (DP) of 6 to 8. Although Kobayashi (Denpun Kagaku; vol. 40, 103–116 (1993)) reported that glucans having only a cyclic structure comprising only an alpha-1,4-glucosidic bond with a DP of more than 9 are synthesized with CGTase, the DP of the largest glucan reported is 13.

Moreover, glucans having only a cyclic structure comprising an alpha-1,4-glucosidic bond with a DP of 9 to 13 are obtained in an extremely low yield, and are not very practical. Also, it is believed that a glucan having a DP of several tens or several hundreds and only a cyclic structure comprising alpha-1,4-glucosidic bonds cannot be synthesized by the reaction of CGTase on starch.

Although a saccharide may be linked to the 6-position of one or more of the glucose residues in cyclodextrin, the maximum size of the saccharide linked is normally up to the size of a maltotetraose in an aspect of the yield. These glucans have a problem in that they are not readily digested by amylases present in digestive secretions such as saliva, pancreatic juice, and the like due to their special structures.

Other enzymes, such as D-enzyme, are not used for the synthesis of glucans having a cyclic structure comprising alpha-1,4-glucosidic bonds.

In methods other than those using the enzymes, the production of glucans having a cyclic structure comprising at least 14 alpha-1,4-glucosidic bonds has not been reported. That is, glucans having a DP of 14 or more, or even several tens or several hundreds and a cyclic structure comprising at least 14 alpha-1,4-glucosidic bonds are not known in the art.

Therefore, the properties of glucans having a DP of 14 or more, or even several tens or several hundreds and a cyclic structure comprising at least 14 alpha-1,4-glucosidic bonds are unknown, and have not been considered as possible substitutes for starches.

Accordingly, starch substitutes, which have such excellent properties in that they have a higher solubility in water than conventional starches, their gelatinized solutions have a lower viscosity, and they are not subject to retrogradation which is observed in the conventional starches have been longawaited.

SUMMARY OF THE INVENTION

This invention overcomes the above-described problems, and provides novel materials having excellent properties, such as a higher solubility in water than conventional starches, solutions having a lower viscosity and which are not subject to retrogradation which is observed in the conventional starches, and which are capable of preventing the retrogradation of starches, and finally are useful as starch substitutes.

The present inventors have found that the enzymes capable of catalyzing the transglycosylation reaction, especially D-enzyme, can catalyze a novel reaction, i.e., the cyclization reaction of an alpha-1,4-glucan in addition to the known disproportionation reaction. Moreover, the present inventors have found that the aforementioned D-enzyme can catalyze the cyclization reaction of an alpha-1,4-glucan having at least one alpha-1,6-glucosidic bond. It is an unknown, unexpected and surprising effect that the D-enzyme can catalyze the synthetic reaction of a glucan having a DP of at least 14 and even several tens or several hundreds and in its molecule one cyclic structure comprising alpha-1,4-glucosidic bonds (i.e., a glucan having in its molecule one cyclic structure comprising at least 14 alpha-1,4-glucosidic bonds). The present inventors have confirmed that the glucans of this invention, which are novel compounds, have an extremely high solubility in water, their solutions have a low viscosity, and they are not subject to retrogradation. The inventors further found that they are useful as food and drink compositions, food additive compositions, or starch substitutes for biodegradable plastics.

The glucan of this invention has in its molecule one cyclic structure comprising at least 14 alpha-1,4-glucosidic bonds.

In a preferred embodiment, the glucan of this invention has only a cyclic structure comprising at least 14 alpha-1,4-glucosidic bonds.

In a preferred embodiment, the glucan of this invention has in its molecule one cyclic structure comprising at least 17 alpha-1,4-glucosidic bonds.

In a preferred embodiment, the glucan of this invention has only a cyclic structure comprising at least 17 alpha-1,4-glucosidic bonds.

In a preferred embodiment, the glucan of this invention has in its molecule one cyclic structure comprising at least 14 alpha-1,4-glucosidic bonds and at least one alpha-1,6-glucosidic bond.

In a preferred embodiment, the glucan of this invention has only a cyclic structure comprising at least 14 alpha-1,4-glucosidic bonds and at least one alpha-1,6-glucosidic bond.

Also, the present invention provides derivatives of said glucans in which at least one of the alcoholic hydroxyl groups of said glucans are derivatized.

In a preferred embodiment, said derivatization is selected from the group consisting of etherification, esterication, crosslinking, and grafting.

Moreover, the present invention provides a process for preparing a glucan or derivative thereof having in its molecule one cyclic structure comprising at least 14 alpha-1,4-glucosidic bonds, including a step of reacting a linear alpha-1,4-glucan or a saccharide containing it with an enzyme capable of producing a glucan having in its molecule one cyclic structure comprising at least 14 alpha-1,4-glucosidic bonds.

In a preferred embodiment, the process of this invention is conducted in the presence of phosphorylase and glucose 1-phosphate.

In a preferred embodiment, the process of this invention is conducted in the presence of an enzyme capable of cleaving an alpha-1,6-glucosidic bond.

In a preferred embodiment, the linear alpha-1,4-glucan or the saccharide containing it used for the process of this invention is at least one selected from the group consisting of malto-oligo saccharides, amylose, amylopectin, glycogen, starches, waxy starches, high amylose starches, soluble starches, dextrins, debranched starches, partially hydrolyzed starches, enzyme synthesized starches with phosphorylase, and the derivatives thereof.

In a preferred embodiment, the enzyme capable of producing said glucan and used in the process of this invention is D-enzyme.

In a preferred embodiment, the enzyme capable of producing said glucan and used in the process of this invention is an immobilized enzyme.

Also, the present invention provides a food and drink composition or a food additive composition including at least one of a glucan or derivative thereof having in its molecule one cyclic structure comprising at least 14 alpha-1,4-glucosidic bonds.

Moreover, the present invention provides an infusion solution including at least one of a glucan or derivative thereof having in its molecule one cyclic structure comprising at least 14 alpha-1,4-glucosidic bonds.

Moreover, the present invention provides an adhesive composition including at least one of a glucan or derivative thereof having in its molecule one cyclic structure comprising at least 14 alpha-1,4-glucosidic bonds.

Moreover, the present invention provides an inclusion material or an adsorption material including (a) at least one of a glucan or derivative thereof having in its molecule one cyclic structure comprising at least 14 alpha-1,4-glucosidic bonds, and (b) a compound to be included or adsorbed therein.

Moreover, the present invention provides a starch including at least one of a glucan or derivative thereof having in its molecule one cyclic structure comprising at least 14 alpha-1,4-glucosidic bonds.

Moreover, the present invention provides an anti-retrogradation agent for starch including at least one of a glucan or derivative thereof having in its molecule one cyclic structure comprising at least 14 alpha-1,4-glucosidic bonds.

The glucans and derivatives thereof this invention, which are novel compounds, have excellent properties in that they have a markedly improved solubility in water compared to conventional starches, such as amylose and amylopectin, and solutions thereof are not subject to retrogradation, which is observed in conventional starches, such as amylose and amylopectin. Moreover, the glucans of this invention may act as an anti-retrogradation agent for starch. Also, aqueous solutions thereof have excellent properties such as having a lower viscosity than the aqueous solutions of conventional starches. Moreover, they have excellent properties in that when heated, with proteins or amino acids, they are not readily colored due to their lower reactivity, compared to conventional starch syrups and dextrins. Also, the glucans and derivatives thereof of this invention have excellent properties, such as including or adsorbing various materials therein. Also, because the glucans and derivatives thereof of this invention have the same basic structure as conventional starches in which the glucose is linked by only an alpha-1, 4-glucosidic bond and an alpha-1,6-glucosidic bond, they are readily decomposed by the enzymes to glucose present in organisms, thereby providing excellent digesting properties and a higher energy exchange efficiency.

Since the process for preparing the glucans and derivatives thereof of this invention includes reacting a starch, a partially decomposed starch, a derivative thereof or a mixture thereof as a raw material with an enzyme capable of producing a glucan having one cyclic structure comprising at least 14 alpha-1,4-glucosidic bonds, the glucans and derivatives thereof of this invention can readily be prepared.

These and other advantages of the present invention will become apparent to those skilled in the art upon reading and understanding the following detailed description with reference to the accompanying figures.

BRIEF DESCRIPTION OF THE DRAWINGS

FIG. 1 is a scheme showing the glucans of this invention.

DESCRIPTION OF THE PREFERRED EMBODIMENTS

Figure 2:
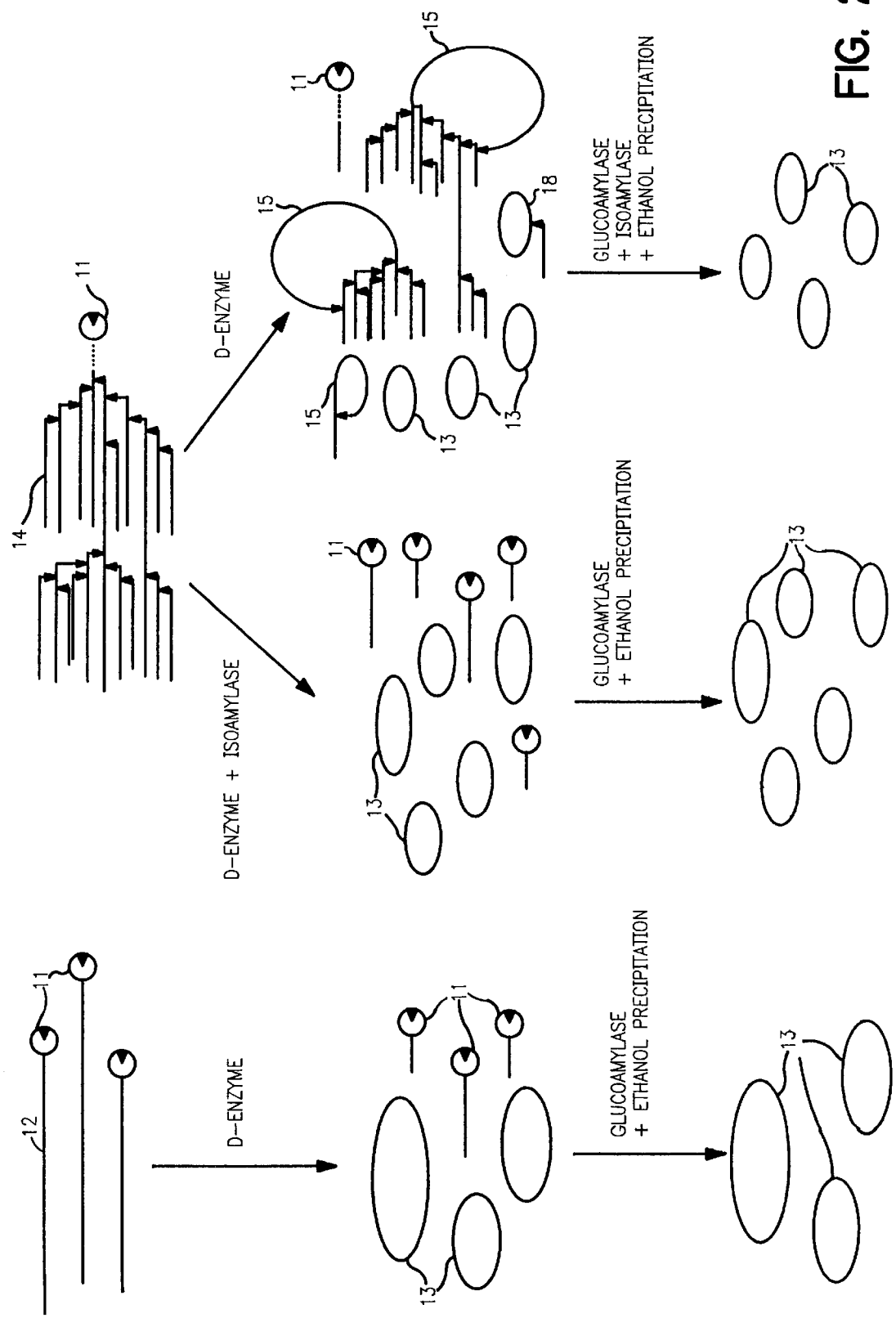
FIG. 2 is a scheme showing a series of steps to produce cyclic glucan having only alpha-1,4-glucosidic bonds from amylose or amylopectin.

The glucans of this invention are those having in their molecules one cyclic structure including at least 14 alpha-1,4-glucosidic bonds, and including specifically various glucans shown schematically in FIG. 1. In FIG. 1, the horizontal straight and curved lines indicate the glucan chains linked by alpha-1,4-glucosidic bonds, and the vertical arrows indicate an alpha-1,6-glucosidic bond (the horizontal straight and curved lines and vertical arrows in the following schemes indicate the same).

As described above, the glucans of this invention include a glucan having only a cyclic structure (hereinafter referred to as the cyclic glucan of this invention), and a glucan having an acyclic structure in addition to a cyclic structure. The cyclic structures include those comprising only alpha-1,4-glucosidic bonds, and those comprising alpha-1,4-glucosidic bonds and at least one alpha-1,6-glucosidic bond. The glucan including at least one alpha-1,6-glucosidic bond within the cyclic structure or in the acyclic structure is produced where a glucan having branch points, such as amylopectin, is used as a substrate.

The glucan having only a cyclic structure can be obtained by treating a glucan having an acyclic structure in addition to a cyclic structure with glucoamylase capable of cleaving the alpha-1,4-glucosidic bond and the alpha-1,6-glucosidic bond from the non-reducing end. Also, it can be obtained directly by using linear alpha-1,4-glucan, or a glucan having branch points as a substrate.

The glucans of this invention have the following properties.

(1) When a glucoamylase (Toyobo, Inc.) which is an exo-type amylase capable of hydrolyzing the alpha-1,4-glucosidic bond and the alpha-1,6-glucosidic bond present in the non-reducing end is reacted on the glucan, a glucoamylase resistant component will remain as a component which is not further degraded. The component is not degraded, even when a phosphatase (Sigma, Inc.) acts thereon, and thereafter the glucoamylase is acted thereon.

(2) The above-described glucoamylase resistant component may be decomposed by an isoamylase (Hayashibara Biochemical Research, Inc.) capable of hydrolyzing the alpha-1,6-glucosidic bond in starch, and may become sensitive to the action of the glucoamylase.

(3) The above-described glucoamylase resistant component is degraded by an alpha-amylase which is an endo-type amylase.

Among the cyclic glucans of this invention, a glucan having only a cyclic structure comprising at least 14 alpha-1,4-glucosidic bonds and no alpha-1,6-glucosidic bond (hereinafter referred to as the cyclic glucan having only alpha-1,4-glucosidic bonds of this invention) has the following properties.

(1) Neither a reducing end nor a non-reducing end is detected in the glucan.

(2) The glucan is not degraded by a beta- amylase (Nagase Biochemical Industries, Inc.) which is an exo-type amylase capable of hydrolyzing the alpha-1,4-glucosidic bond from a non-reducing end, or a glucoamylase (Toyobo Inc.).

(3) The glucan is not degraded by the combined use of an isoamylase (Hayashibara Biochemical Research, Inc.) capable of hydrolyzing the alpha-1,6-glucosidic bond in starch and a pullulanase (Hayashibara Biochemical Research, Inc.), or the combined use of isoamylase, pullulanase, and a beta-amylase.

(4) The glucan is completely degraded by an alpha-amylase (Nagase Biochemical Industries, Inc.) which is an endo-type amylase capable of hydrolyzing the alpha-1,4-glucosidic bond within a starch molecule.

(5) When the glucan is hydrolyzed by a bacterial saccharification-type alpha-amylase (Nagase Biochemical Industries, Inc.) and analyzed by HPLC, only glucose, maltose, and a slight amount of maltotriose are obtained. That is, no bond, other than alpha-1,4-glucosidic bonds is present in the glucan.

Among the cyclic glucans of this invention, a glucan having only a cyclic structure including at least 14 alpha-1,4-glucosidic bonds and at least one alpha-1,6-glucosidic bond (hereinafter referred to as the cyclic glucan having an alpha-1,6-glucosidic bond of this invention) has the following properties.

(1) Neither a reducing end nor a non-reducing end is detected in the glucan.

(2) The glucan is not degraded by a beta-amylase (Nagase Biochemical Industries, Inc.) which is an exo-type amylase capable of hydrolyzing the alpha-1,4-glucosidic bond from a non-reducing end, or a glucoamylase (Toyobo, Inc.).

(3) The glucan is degraded by an isoamylase (Hayashibara Biochemical Research, Inc.) capable of hydrolyzing the alpha-1,6-glucosidic bond in starch, and then becomes sensitive to the action of the glucoamylase.

(4) The glucan is degraded by an endo-type alpha-amylase (Nagase Biochemical Industries, Inc.) capable of hydrolyzing the alpha-1,4-glucosidic bond in starch, and then becomes sensitive to the glucoamylase. Also, it is known that the smallest limit dextrin is isomaltosyl-maltose (IMM), where the endo-type alpha-amylase acts on the glucan having alpha-1,6-glucosidic bond (Yamamoto T., Handbook of amylase and related enzymes, Pergamon press, p. 40–45 (1988)). The IMM is detected when the above-described cyclic glucan having an alpha-1,6-glucosidic bond is treated with endo-type alpha-amylase.

The number of the glucosyl residue which constitute the cyclic structure of the glucan of this invention are at least 14, preferably 14 to about 5000, and more preferably about 17 to 1000. Where the glucan has alpha-1,6-glucosidic bonds, the numbers of the alpha-1,6-glucosidic bonds may be at least one, usually 1 to 500, and preferably 1 to about 100.

The determination of the aforementioned reducing ends may be conducted by the modified Park-Johnson method (Hizukuri, et al., (1981) Carbohydr. Res: 94; 205–213), and the determination of the non-reducing ends may be conducted by the rapid Smith-degradation method (Hizukuri and Osaki, (1978) Carbohydr. Res: 63; 261–264).

The decomposition of the glucan with the aforementioned beta-amylase and glucoamylase which are exo-type amylases, or isoamylase, pullulanase, or alpha-amylase which are endo-type amylases, may be analyzed by, for example, dissolving the glucan of this invention having only a cyclic structure at least 14 alpha-1,4-glucosidic bonds in distilled water so that the concentration is 0.1% (w/v), reacting 100 μl of the solution with a suitable amount of the above-described enzyme at 30°–45° C. for several hours, and subjecting the reaction product to the carbohydrate analysis system of DIONEX, Inc. (pump system: DX300, detector: PAD-2, column: CarboPacPA100). The elution procedure may be conducted under the conditions of, for example, flow rate: 1 ml/min., NaOH concentration: 150 mM, sodium acetate concentration: 50 mM at 0 minute, 50 mM at 2 minutes, 350 mM at 37 minutes, 850 mM at 45 minutes, and 850 mM at 47 minutes to analyze the DP and the saccharide produced.

The detection of the aforementioned glucoamylase resistant component from the glucans or derivatives thereof of this invention may be conducted as follows. For example, 100 mg of the glucan of this invention are dissolved in 5 ml of distilled water, to which glucoamylase is added so that the final concentration is 10 units/ml, and reacted overnight at 40° C. After heating the reaction product at 100° C. for 10 minutes and centrifuging it to remove the insoluble materials, a 10-fold volume of ethanol is added to the reaction product and centrifuged to recover the remaining polysaccharides as a precipitate. The precipitate is further dissolved in 1 ml of distilled water, to which a glucoamylase is added so that the final concentration is 50 units/ml, reacted at 40° C. for 1 hour, heated at 100° C. for 10 minutes, and centrifuged to remove any insoluble materials. To the reaction product, a 10-fold volume of ethanol is added to obtain a precipitate. When a starch, which is partially modified with a phosphate group, is used as a raw material for the glucan of this invention, the resulting precipitate is dissolved in a 10 mM carbonate buffer (pH 9.4, containing 10 mM of $MgCl_2$ and 0.3 mM of $ZnCl_2$), to which 20 units of a phosphatase (derived from bovine, Sigma, Inc.) are added, and reacted at 40° C. for 24 hours. Thereafter, a 10-fold volume of ethanol is added to the reaction product to recover a precipitate. The precipitate is dissolved again in distilled water, to which a glucoamylase is added so that the final concentration is 50 units/ml, and reacted at 40° C. for 1 hour. Then, a 10-fold volume of ethanol is added to the reaction product to obtain the glucoamylase resistant component as a precipitate.

The determination of the acyclic structure, the cyclic structure having alpha-1,6-glucosidic bonds, and the cyclic structure having only alpha-1,4-glucosidic bonds may be conducted as follows. After dissolving 10 mg of the glucan sample in 1 ml of DMSO, the solution is immediately diluted by using 8 ml of a 100 mM sodium acetate buffer. Four 900 μl samples are picked up from the diluted solution, and to each sample, 100 μl of each of distilled water, a glucoamylase solution, a solution containing debranching enzyme and glucoamylase, and a solution containing an endo-type alpha-amylase and glucoamylase are added, and reacted at 40° C. for 4 hours. After the reaction is terminated by boiling, the resulting glucose is measured by using a commercially available glucose quantitation kit to calculate the number of the acyclic structure, the cyclic structure having alpha-1,6-glucosidic bonds, and the cyclic structure having only alpha-1,4-glucosidic bonds in the glucan sample. Further details of the determination are illustrated in the examples.

The DP of the cyclic structure in the glucans of this invention can be measured by chromatography. It is generally known that a cyclic polysaccharide behaves differently on chromatography compared to a linear polysaccharide having the same DP. The identification of the cyclic structure and the determination of the DP of the cyclic polysaccharide may be conducted using this property. For example, the cyclic glucan having only alpha-1,4-glucosidic bonds of this invention, which is obtained by reacting with a D-enzyme, is separated by the above-described carbohydrate analysis system of DIONEX, Inc. to obtain a single peak fraction.

After treating the resulting fraction with, for example, a 0.1N HCl at 100° C. for 30 minutes to hydrolyze partially its cyclic structure, the resulting linear glucans having various DPs are analyzed by the carbohydrate analysis system of DIONEX, Inc. to determine their DPs. The detailed analysis of this procedure is described in the examples.

The glucans of this invention are obtained by reacting a linear alpha-1,4-glucan or a saccharide containing it with an enzyme capable of producing a glucan having in its molecule one cyclic structure including at least 14 alpha-1,4-glucosidic bonds. Any enzymes may be used so long as they have such activity. It is preferred to use a D-enzyme in this invention.

The D-enzyme which was initially discovered in potato is known to be present in various plants, and microorganisms such as *E. coli*. Therefore, any D-enzymes, such as those obtained by expressing a gene coding for an enzyme from plants in a host such as *E. coli*, may also be used, regardless of their origin. The following examples disclose, but are not limited to, a process for purifying D-enzymes from potato and *E. coli*.

A process for purifying D-enzyme from potato is described in Takaha, et al., *J. Biol. Chem.* vol. 268, 1391–1396 (1993). First, a potato tuber is homogenized in a suitable buffer containing 5 mM of mercaptoethanol, centrifuged, passed through a 0.45 μm membrane, and thereafter loaded onto a Q-Sepharose column, and washed with, for example, a buffer of (1) a 20 mM Tris-HCl (pH 7.5) containing 5 mM 2-mercaptoethanol (buffer A) and (2) 150 mM NaCl. The D-enzyme is eluted into buffer A containing 450 mM NaCl. The eluate is dialyzed, to which an ammonium sulfate is added so that the final concentration is 500 mM, and loaded onto a Phenyl Toyopearl 650M column (Toso, Inc.), and eluted by varying the ammonium sulfate concentration in buffer A from 500 mM to 0 mM. The D-enzyme active fractions are collected and dialyzed against buffer A. The dialyzed solution is loaded onto a PL-SAX column (Polymer Laboratory, U.K.) which is equilibrated with buffer A, and eluted by varying the NaCl concentration added to buffer A between 150 mM and 400 mM to collect the D-enzyme active fractions. The D-enzyme may be also purified from potato by the above-described procedure. The measurement of enzyme activity is illustrated in detail in the examples.

Aforementioned Takaha, et al., *J. Biol. Chem.* vol. 268, 1391–1396 (1993) discloses the cDNA sequence of the potato D-enzyme (page 1394, FIG. 3), the production of the recombinant plasmid of the D-enzyme (page 1392), the expression of said recombinant plasmid in *E. coli*, and the purification of the D-enzyme from the recombinant *E. coli*. The D-enzymes produced by the recombinant method can also be used in this invention. According to the process for purifying the D-enzyme from *E. coli*, for example, after cultivating an *E. coli* TG-1 strain at 37° C. up to the logarithmic growth phase using a LB liquid medium, maltose is added to the medium so that the final concentration is 1% (w/v), and further cultivated at 37° C. for 2 hours. The medium is centrifuged to collect the bacteria. The bacteria are suspended in the aforementioned buffer A, subjected to ultrasonication, and centrifuged to obtain a bacterial extract. Then, the bacterial extract is loaded onto, for example, a Q-Sepharose Fast Flow column (Pharmacia, Inc.) which is equilibrated with buffer A, and eluted by varying the NaCl concentration added to buffer A from 0 mM to 500 mM to collect the D-enzyme active fractions. To the collected active fraction, ammonium sulfate is added so that the final concentration is 1M, allowed to stand, and centrifuged to remove any insoluble precipitate. The supernatant is loaded onto a Phenyl Toyopearl 650M column (Toso, Inc.) which is equilibrated with buffer A containing 1M ammonium sulfate. The D-enzyme is eluted by varying the ammonium sulfate concentration added to buffer A from 1M to 0 mM, then the D-enzyme active fraction is collected. After dialyzing the fraction against buffer A, the dialyzed solution is loaded onto a Resource Q column (Pharmacia, Inc.) which is equilibrated with buffer A, and the D-enzyme is eluted by varying the NaCl concentration added to buffer A from 0 mM to 500 mM to purify the D-enzyme.

The D-enzyme may be purified as described above. Unless an endo-type amylase, which acts on the alpha-1,4-glucosidic bond in a starch molecule, is detected in the D-enzyme preparation, any crude D-enzymes preparation in any purification step may be used for the synthesis of the glucans of this invention.

Also, the enzyme used for the synthesis reaction of the glucans of this invention may be an immobilized enzyme, whether it is a purified enzyme or a crude enzyme, and the reaction procedure may be of a batch type or a continuous system. Processes for immobilizing the enzyme that can be used include carrier bonding methods (for example, covalent bonding methods, ionic bonding methods, and physical adsorption methods), crosslinking and entrapping methods (including those of matrix types and microcapsule types), and the like.

In order to obtain only the cyclic glucan of this invention having only alpha-1,4-glucosidic bonds, it may be prepared by the action of the above-described enzyme that can be used for the glucan of this invention, for example, D-enzyme, on a linear alpha-1,4-glucan consisting of only alpha-1,4-glucosidic bonds, for example, amylose, a debranched starch, an enzyme synthesized amylose with phosphorylase, malto-oligosaccharide, and the like.

Also, the cyclic glucan of this invention having only alpha-1,4-glucosidic bonds when a saccharide having an alpha-1,6-branched structure, such as, amylopectin, glycogen, starches, waxy starches, high amylose starches, soluble starches, dextrins, hydrolyzed starches, enzyme synthesized amylopectins with phosphorylase, and the like is used as a raw material, may be prepared by reacting directly the above-described enzyme that can be used for the glucan of this invention, for example, D-enzyme with the saccharide. The glucan may also be prepared by reacting the above-described saccharide with the above-described enzyme that can be used for the glucan of this invention, for example, a D-enzyme in the presence of an enzyme is capable of cleaving the alpha-1,6-glucosidic bonds, but unable to cleave alpha-1,4-glucosidic bonds, for example, isoamylase, pullulanase, and the like.

For example, as described in FIG. 2, the amylose (12) having the reducing end (11) is reacted with the D-enzyme to prepare the above-described cyclic glucan (13) having only alpha-1,4-glucosidic bonds, and thereafter is hydrolyzed successively from the non-reducing end with the addition of glucoamylase. Then, ethanol is added to the hydrolyzed product to recover a cyclic glucan as a precipitate which is thereafter freeze-dried to obtain the cyclic glucan (13) having only alpha-1,4-glucosidic bonds.

Also, the amylopectin (14) having the reducing end (11), isoamylase incapable of cleaving an alpha-1,6-glucosidic bonds, and the D-enzyme are reacted simultaneously to prepare the cyclic glucan (13) having only alpha-1,4-glucosidic bonds, and thereafter is hydrolyzed successively from the non-reducing end with the addition of glucoamylase. Then, ethanol is added to the hydrolyzed product to recover a cyclic glucan as a precipitate which is thereafter freeze-dried to obtain the cyclic glucan (13) having only alpha-1,4-glucosidic bonds.

Also, the amylopectin (14) having the reducing end (11) is reacted with the D-enzyme to prepare the cyclic glucan (13) having only alpha-1,4-glucosidic bonds, the glucan (18) having a cyclic structure including only alpha-1,4-glucosidic bonds and an acyclic structure, and the glucan (15) having in its molecule one cyclic structure including at least 14 alpha-1,4-glucosidic bonds and at least one alpha-1,6-glucosidic bond, and thereafter reacting with glucoamylase and isoamylase, and possibly further be reacting with pullulanase. Then, ethanol is added to the reaction product to precipitate a cyclic giucan which is recovered and thereafter freeze-dried to obtain the cyclic glucan (13) having only alpha-1,4-glucosidic bonds.

Moreover, a glucan having in its molecule one cyclic structure including at least 14 alpha-1,4-giucosidic bonds and at least one alpha-1,6-glucosidic bond (he reinafter referred to as the glucan having alpha-1,6-glucosidic bonds of this invention) may be prepared by the action of the above-described enzyme that can be used for the glucans of this invention, for example, D-enzyme on a raw material having an alpha-1,6-branched structure, such as, amylopectin, glycogen, starches, waxy starches, high amylose starches, soluble starches, dextrins, hydrolyzed starches, enzyme synthesized amylopectins with phosphorylase, and the like.

Figure 3:
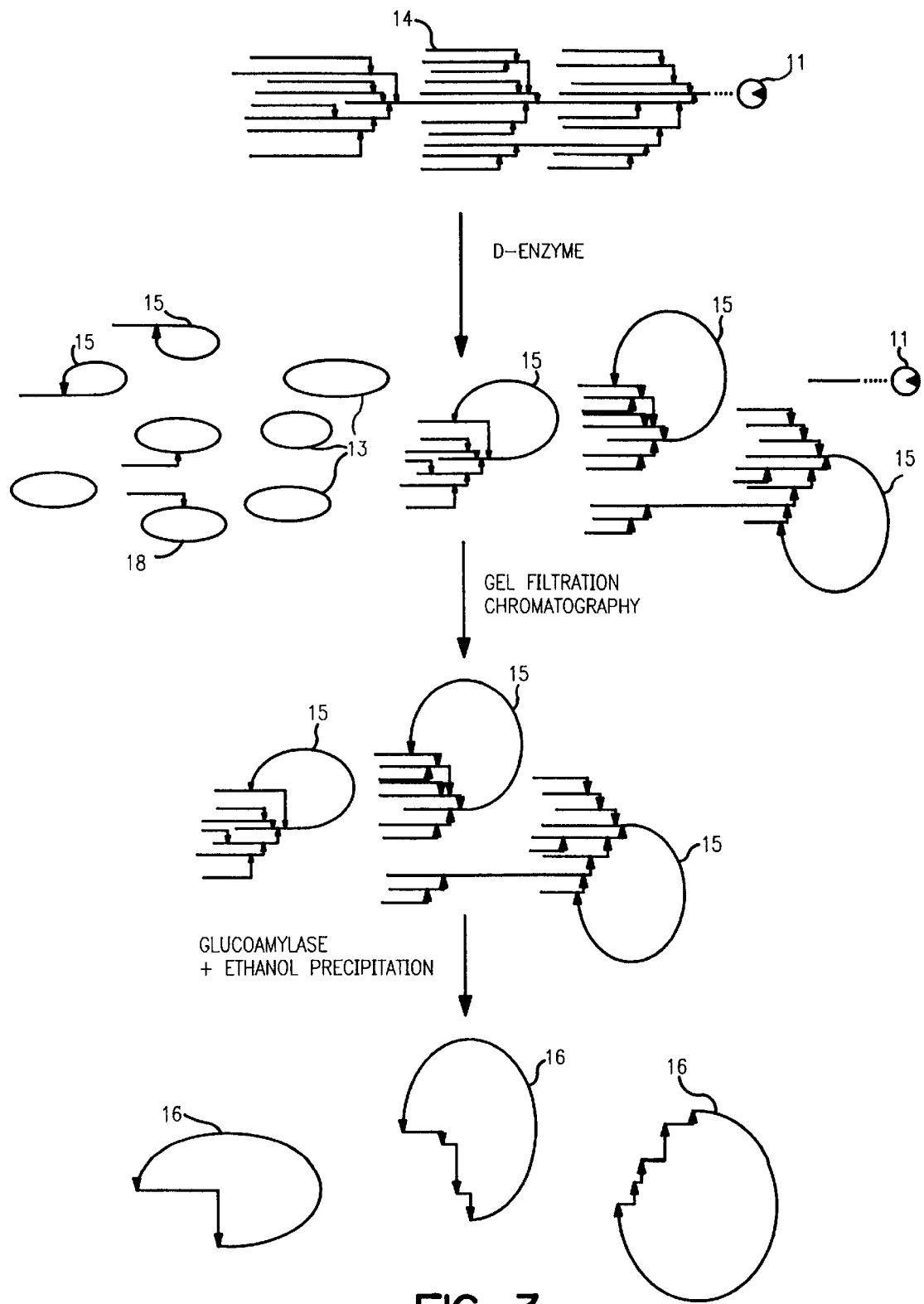
FIG. 3 is a scheme showing a series of steps to produce glucan having only a cyclic structure comprising at least one alpha-1,6-glucosidic bonds from amylopectin.

For example, as described in FIG. 3, the amylopectin (14) having the reducing end (11) is reacted with the D-enzyme to prepare the glucan (15) having in its molecule one cyclic structure including at least 14 alpha-1,4-glucosidic bonds and at least one alpha-1,6-glucosidic bond, the cyclic glucan (13) having only alpha-1,4-glucosidic bonds and the glucan (18) having a cyclic structure including only alpha-1,4-glucosidic bonds and an acyclic structure. Thereafter, the above-described glucan (15) having in its molecule one cyclic structure including at least 14 alpha-1,4-glucosidic bonds and at least one alpha-1,6-glucosidic bond may be separated by gel filtration chromatography. To the glucan (15), glucoamylase is added to hydrolyze successively the acyclic structure from the non-reducing end. After hydrolysis, ethanol is added to the hydrolyzed product to recover a cyclic glucan as a precipitate which is thereafter freeze-dried to obtain the glucan (16) having only a cyclic structure including at least one alpha-1,6-glucosidic bond.

The linear alpha-1,4-glucans and saccharides containing them that can be used in this invention include maltooligosaccharides such as maltotriose, maltotetraose, maltopentaose, and the like; amylose, amylopectin, glycogen, starches, waxy starches, high amylose starches, soluble starches, dextrins, debranched starches, partially hydrolyzed starches, enzyme synthesized starches with phosphorylase, and derivatives thereof. These may be used alone, or combined together. The debranched starch indicates a material obtained by enzymatically cleaving wholly or partially the alpha-1,6-glucosidic bonds present in starches. Also, the partially hydrolyzed starch indicates a material obtained by cleaving enzymatically or chemically a portion of the alpha-1,4-glucosidic bonds present in starches. The raw materials for partially hydrolyzed starches that can be used include, for example, amylopectins having a DP of about 100 or more, amyloses having a DP of about 20 or more, and the like.

Also, the linear alpha-1,4-glucan or the saccharide containing it that can be used in this invention may be reacted with an enzyme capable of producing a glucan having in its molecule one cyclic structure including at least 14 alpha-1, 4-glucosidic bonds in the presence of phosphorylase and glucose 1-phosphate. The phosphorylase can catalyze the extension reaction of the alpha-1,4-glucan chain where an excess amount of the glucose 1-phosphate is present. Thus, where the alpha-1,4-glucan chain of the above-described raw material does not have a sufficient length to undergo the cyclization reaction with the above-described enzyme, the yield of the glucan of this invention may be increased by coexisting the phosphorylase and glucose 1-phosphate.

Moreover, the derivatives of the above-described starches and partially hydrolyzed starches, for example, the derivatives of the above-described starches in which at least one alcoholic hydroxyl group is etherified (carboxy-methylated, hydroxyalkylated, etc.), esterified (phosphorylated, acetylated, sufurized, etc.), crosslinked, or grafted may also be used as raw materials. Mixtures of two or more of these may also be used as the raw materials.

The reaction of the above-described raw materials with the enzyme that can be used in this invention may be carried out under any conditions of pH, temperature, etc., so long as the glucans of this invention are produced under such conditions.

When the D-enzyme is used, for example, the pH of the reaction mixture is normally about 3 to about 10, and preferably about 4 to about 9, and more preferably 6 to 8 in view of the reaction rate and efficiency, the stability of the enzyme, and the like. The temperature is in the range of from about 10° to about 90° C., preferably from about 20° to about 60° C., and more preferably, from 30° to 40° C. in view of the reaction rate and efficiency, the stability of the enzyme, and the like. In the case of using an enzyme obtained from heat resistant microorganisms, it may be used at an elevated temperature of from about 50° to about 90° C. The concentration of the above-described raw material (substrate concentration) may be determined in view of the DP of the substrate used, and is normally about 0.1 to about 30%, preferably about 0.1 to about 10% in light of the reaction rate and efficiency, the readiness of the handling of the substrate solution, and the like, and more preferably about 0.5 to about 5% in view of the solubility of the substrate. The amount of the enzyme employed may be determined in connection with the reaction time, and the concentration of the substrate, and is preferably selected so that the reaction is terminated in about 1 hour to about 48 hours, and usually about 50 to about 10,000 units per 1 g of the substrate, preferably about 70 to about 2,500 units per 1 g of the substrate, more preferably about 400 to about 2,000 units per 1 g of the substrate.

The glucans of this invention may be separated and purified by applying any known methods. For example, after the above-described reaction is terminated, the glucans of this invention may be separated and purified by the precipitation with a solvent, or the separation with a membrane, chromatography, and the like. Preferably, they are purified as such, or by heating the reaction solution. The glucan of this invention having only alpha-1,4-glucosidic bonds may be subjected to separation or purification methods, such as precipitation with a solvent, membrane separation, chromatography separation, and the like, after adding an exo-type beta-amylase or glucoamylase to the reaction solution to degrade the remaining linear alpha-1,4-glucan, or in the case where a branched polysaccharide such as starch is used, with an enzyme capable of cleaving the alpha-1,6-glucosidic bond thus leaving only the cyclic alpha-1,4-glucan.

Also, the glucans of this invention may readily be etherified, esterified, crosslinked or grafted to obtain their derivatives which can be utilized for the above-described purposes and uses. The methods for the derivatization that can be used include those which are usually used for the modification of starch (See, Seibutsu Kagaku Jikkenho 19, "Experimental Methods for Starches and Related Saccharides", Nakamura, et al., Gakkai Shuppan Center, 1986, pages 273–303). For example, phosphorylated glucan of this invention is obtained by reacting the glucan of this invention with phosphorus oxychloride in dimethylformamide.

The glucans of this invention obtained as described above, which are novel compounds, have markedly improved solubility in water, compared to conventional starches, such as amylose, and amylopectin; and their aqueous solutions have excellent properties in that they are not subject to retrogradation which is observed in the aqueous solutions of conventional starches, such as amylose and amylopectin. Also, the glucans of this invention have the effect of controlling or preventing the retrogradation of conventional starches. Moreover, their aqueous solutions have excellent properties, such as having a lower viscosity than the aqueous solutions of conventional starches. Moreover, when the glucans of this invention are heated, such as when mixed with a protein or amino acid, they are not readily colored due to their lower reactivity, as compared to conventional starch syrups and dextrins. Also, the glucans of this invention have excellent properties, such as including or adsorbing various materials. Also, because the glucans of this invention have the same basic structure as conventional starches in which the glucose is linked by only alpha-1,4-glucosidic bonds and alpha-1,6-glucosidic bonds, they are readily degraded to glucose by the enzymes present in organisms, thereby providing excellent digesting properties and higher energy exchange efficiency.

Due to the properties of the glucans of this invention, they can be used for any foods in which conventional starches, dextrins are employed, including most food and drink compositions and food additive compositions. "Food and drink composition" is a general term including human foods, animal feeds, and pet foods. That is, the glucans can effectively be utilized for liquid or powder drinks such as coffee, tea, Japanese tea, oolong tea, juices, sports drinks, and the like; wheat products such as breads, cookies, crackers, biscuits, cakes, pizzas, pies, and the like; pastas such as spaghetti, macaroni, and the like; noodles such as Japanese noodles, Chinese noodles, and the like; candies such as caramels, gums, chocolates, and the like; snacks such as rice crackers, potato chips, other snacks, and the like; ices such as ice creams, sherbets, and the like; milk products such as creams, margarines, cheeses, milk powders, condensed milks, milk beverages, and the like; western desserts such as jellies, puddings, mousses, yogurts, and the like; Japanese desserts such as bean cakes, rice jellies, rice cakes, rice bean cakes, and the like; condiments such as soy sauces, soy sauce dips, noodle soups, Worcester sauces, broth bases, stew bases, soup bases, combined condiments, curry bases, mayonnaise, dressings, ketchup, and the like; retort foods and canned foods for curry, stew, soups, rice bowl bases, and the like; refrigerated foods and frozen foods such as hams, hamburgers, meat balls, croquettes, pilafs, rice balls, and the like; processed seafoods such as fish sticks and fish pastes, and the like; rice products such as rice balls, lunch rice, sushi rice, and the like; gyoza skins, shumai skins, and the like. Moreover, because the glucans have improved digestive properties, they can be used for formulae, baby foods, pet foods, animal feeds, sports drinks, sports foods, nutrient supplemental foods, and the like. The glucans of this invention can be used for infusion solutions.

The glucans of this invention can be used for adhesive compositions. The glucans of this invention possess adhesiveness and tenacity, and therefore are available for the fields in which the conventional starches, dextrins and derivatives thereof are employed. The adhesive compositions include, for example, surface sizing agents, coating agents, layer adhesives, and the like in the paper manufacturing and processing industries; binding agents, and the like in the food industries; pastes, bonds, and the like in the textile and building material industries.

The glucans of this invention include or adsorb various materials. Although cyclodextrins and the conventional amyloses have inclusion and adsorption abilities, because the glucans of this invention have a significantly higher solubility in water than conventional amyloses and cyclodextrins, they are expected to be applicated to a broader range of fields. Also, since they have a higher DP than the cyclodextrins, it is thought that they have a different guest specificity from that of the cyclodextrins. The inclusion or adsorption of a material into amyloses or cyclodextrins may result in the change of its properties and the acquisition of new properties. These properties that are well known include, for example, improved solubility, non-volatilization of volatile materials, stabilization of unstable materials, masking of offensive odors, and the like. The materials which are adsorbed or included into the glucans of this invention include, but are not specifically limited to, for example, foods such as Japanese horseradish, soy sauce, Japanese tea, Japanese pepper, citron, spices, condiments, coloring matters, and the like; medicines such as menthol, linoleic acid, and the like. The inclusion and adsorption materials thus prepared can be used as foods and medicines. For example, they can be utilized for the above-described foods, bath crystals, and medicines such as internal medicines, powder medicines, and the like.

The glucans of this invention may be used as raw materials for biodegradable plastics, and raw materials in starch industries such as intermediate materials in the production of cyclodextrins from starches, and the like, as focusing on the lower viscosity of their solutions.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

EXAMPLES

The following examples specifically illustrate the glucans of this invention, however, the scope of this invention is not limited to these examples.

Example 1

Preparation of D-enzyme

D-enzyme is purified according to the procedure described in Takaha, et al., *J. Biol. Chem.* vol. 268, 1391–1396 (1993). First, a potato tuber was homogenized in 20 mM Tris-HCl (pH 7.5) buffer containing 5 mM 2-mercaptoethanol (buffer A), centrifuged, passed through a 0.45 μm membrane, loaded onto a Q-Sepharose column (16×100 mm; Pharmacia, Inc.), and washed with buffer A containing 150 mM NaCl. The D-enzyme was eluted into buffer A containing 450 mM NaCl. The eluate was dialyzed against buffer A, to which ammonium sulfate was added so that the final concentration was 500 mM. This solution was loaded onto a Phenyl Toyopearl 650M column (10×100 mm; Toso, Inc.), and eluted by varying the ammonium sulfate concentration in buffer A from 500 mM to 0 mM. The D-enzyme active fraction was collected, and dialyzed against buffer A. The dialyzed solution was concentrated using the Amicon Centricon 30 microconcentrator, loaded onto a PL-SAX HPLC column (Polymer Laboratory, U.K.), and eluted by a linear gradient of NaCl concentration of 150–400 mM added to the buffer A to collect the D-enzyme active fraction which was thereafter concentrated using the above-described Amicon Centricon 30 microconcentrator.

D-enzyme activity was assayed in a 100 $\mu$l reaction mixture containing 100 mM Tris-HCl buffer (pH 7.0), 5 mM 2-mercaptoethanol, 1% (w/v) maltotriose and the enzyme. The reaction mixture was incubated at 37° C. for 10 min and terminated by immersing the reaction tubes in boiling water for 3 min. Released glucose was measured by the glucose oxidase method (Barham and Trinder, (1972) Analyst 97; 142). One unit of D-enzyme activity is defined as the amount of enzyme which produces 1 $\mu$mol of glucose per min under these assay conditions.

Example 2
Preparation of the cyclic glucan having only alpha-1,4-glucosidic bonds of this invention After dissolving completely 500 mg of the commercially available amylose (having an average molecular weight of 30,000) in 10 ml of 1N—NaOH, 10 ml of 1M Tris hydrochloric acid buffer (pH 7.5), 20 ml of distilled water, and 10 ml of 1N—hydrochloric acid were added successively to the solution to prepare an amylose solution. Two hundred units of the D-enzyme from potato were added to the amylose solution, and reacted at 30° C. for 24 hours.

After centrifuging the reaction solution, the supernatant was treated at 100° C. for 5 minutes, and centrifuged again to remove the denatured enzyme protein. To the supernatant, about 100 units of beta-amylase and 100 units of glucoamylase were added and reacted at 50° C. for 3 hours, and thereafter precipitated with the addition of a 10-fold amount of ethanol. The precipitate was freeze-dried to obtain about 400 mg of powder.

Example 3
Preparation of the cyclic glucan having only an alpha-1,4-glucosidic bond of this invention After dissolving completely 500 mg of the commercially available soluble starch in 10 ml of 1N—NaOH, 10 ml of 1M Tris hydrochloric acid buffer (pH 7.5), 20 ml of distilled water, and 10 ml of 1N—hydrochloric acid were added successively to the solution to prepare a starch solution. Ten units of the commercially available isoamylase and 200 units of the D-enzyme from potato were added to the starch solution, and reacted at 30° C. for 24 hours.

After centrifuging the reaction solution, the supernatant was treated at 100° C. for 5 minutes, and centrifuged again to remove the denatured enzyme protein. To the supernatant, about 100 units of beta-amylase and 100 units of glucoamylase were added and reacted at 50° C. for 3 hours, and thereafter a cyclic glucan was precipitated with the addition of a 10-fold amount of ethanol. The precipitate was freeze-dried to obtain about 150 mg of the powder of the cyclic glucan having only alpha-1,4-glucosidic bonds.

Example 4
Preparation of the cyclic glucan having only alpha-1,4-glucosidic bonds of this invention After dissolving completely 20 mg of the commercially available amylose (having an average molecular weight of 320000) in 1 ml of DMSO, 9 ml of 20 mM citric acid buffer (pH 7.0) containing 68 units of the D-enzyme purified in Example 1 were added, and reacted at 30° C. for 10 minutes, 20 minutes, 30 minutes, 2 hours, 6 hours and 18 hours. The reaction solutions were heated at 100° C. for 10 minutes, and centrifuged to remove the denatured enzyme protein. Five units of glucoamylase were added to 1 ml of the supernatants, and reacted at 40° C. for 4 hours to remove the linear amylose. Then, the reaction solutions were heated again at 100° C. for 10 minutes, and thereafter centrifuged to remove the modified enzyme protein. To 250 $\mu$l of the supernatants, 10-fold of ethanol were added to precipitate the cyclic glucans.

Example 5
Identification of the cyclic glucan having only alpha-1,4-glucosidic bonds (1) Quantitation of the reducing ends and non-reducing ends The quantitation of the reducing ends of the powder obtained in Example 2 is conducted according to the Park-Johnson method described in Hizukuri, et al. (1981) Carbohydr. Res: 94: 205–213. The quantitation of the non-reducing ends of the powder is conducted according to the rapid Smith-degradation method described in Hizukuri and Osaki (1978) Carbohydr. Res: 63: 261–264. As a result, neither a reducing end nor a non-reducing end was detected in the powder.

(2) Digestion of the glucans with the exo-type enzyme and debranching enzyme

Figure 4:
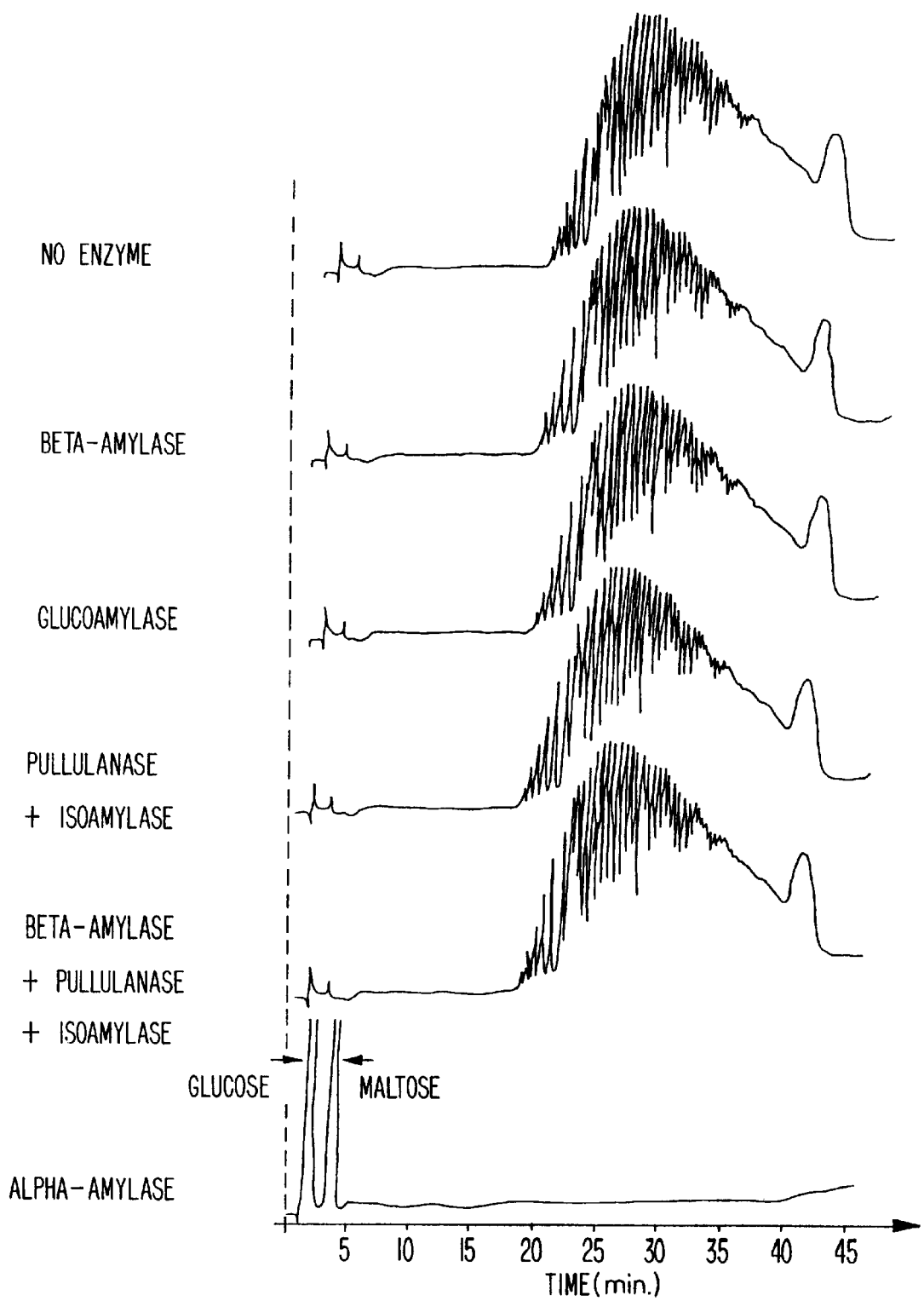
FIG. 4 shows elution patterns of the cyclic glucan of this invention having only alpha-1,4-glucosidic bonds after treatment with or without starch hydrolases.

After dissolving the powder obtained in Example 2 in distilled water so that the concentration is 0.1% (w/v), 1 unit of each of the following amylases was added to 100 $\mu$l of the aqueous solution, and reacted at 40° C. for 2 hours. The reaction product was analyzed by the carbohydrate analysis system of DIONEX, Inc. (pump system: DX300, detector: PAD-2, column: CarboPacPA100). The elution procedure was conducted under the conditions of flow rate: 1 ml/min., NaOH concentration: 150 mM, sodium acetate concentration: 50 mM at 0 minute, 50 mM at 2 minutes, 350 mM at 37 minutes (gradient curve No.3), 850 mM at 45 minutes (gradient curve No.7), and 850 mM at 47 minutes. FIG. 4 shows the results.

As shown in FIG. 4, the powder obtained in Example 2 was not degraded by the beta-amylase (Nagase Biochemical Industries, Inc.) and glucoamylase (Toyobo Co., Ltd.) which are exo-type amylases capable of hydrolyzing the alpha-1, 4-glucosidic bond from the non-reducing end of a starch molecule. Also, it was not degraded by a combined use of the isoamylase (Hayashibara Biochemical Research, Inc.) and the pullulanase (Hayashibara Biochemical Research, Inc.) which are capable of hydrolyzing the alpha-1,6-glucosidic bond in starch, or a combined use of the isoamylase, pullulanase and beta-amylase. However, the powder was completely degraded by the alpha-amylase (Nagase Biochemical Industries, Inc.) which is an endo-type amylase capable of hydrolyzing the alpha-1,4-glucosidic bond within the starch molecule.

(3) Digestion of the glucans with the endo-type enzyme

After dissolving the powder obtained in Example 2 in distilled water so that the concentration was 0.1% (w/v), 1 unit of a bacterial saccharification-type amylase (Nagase Biochemical Industries, Inc.) was added to 100 $\mu$l of the aqueous solution, and reacted at 40° C. for 2 hours. When the reaction product was analyzed by HPLC, only glucose, maltose, and a slight amount of maltotriose were obtained. This indicates that the powder obtained in Example 2 contains only alpha-1,4-glucosidic bonds and that the resulting powder is a cyclic glucan having only alpha-1,4-glucosidic bonds.

The same analysis indicates that the powders obtained in Examples 3 and 4 are cyclic glucans having only alpha-1,4-glucosidic bonds.

Example 6

Measurement of the DP of the cyclic glucan having only alpha-1,4-glucosidic bonds It is generally known that a cyclic glucan elutes differently compared to a linear glucan having the same DP on several chromatographies. The identification of the cyclic structure, and the determination of the DP of the cyclic glucan are achieved by the use of this property.

(1) Preparation of the cyclic glucan having a specific DP and only alpha-1,4-glucosidic bonds Since the material obtained in Example 2 is considered to be a mixture of cyclic glucans having various DPs and only alpha-1,4-glucosidic bonds, the material is purified to obtain a cyclic glucan having a specific DP.

Figure 5:
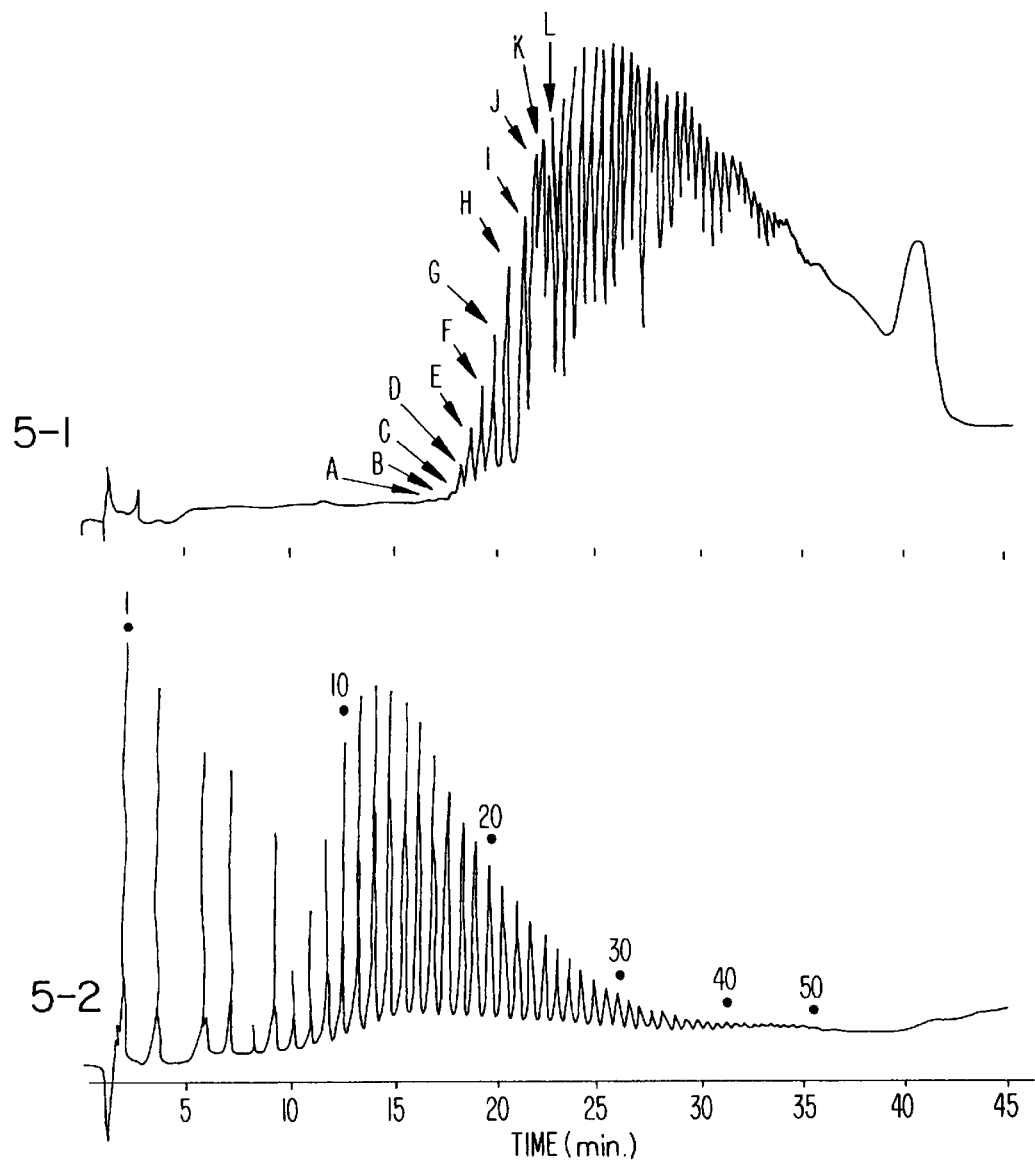
FIG. 5 shows elution patterns of the glucans, wherein 5-1 is an elution pattern of the cyclic glucan having only alpha-1,4-glucosidic bonds obtained in Example 2, and 5-2 is an elution pattern of the linear alpha-1,4-glucans. The numbers in each peak indicate the DP.

FIG. 5-1 shows the elution pattern when 100 μg of the material obtained in Example 2 was analyzed by the carbohydrate analysis system of DIONEX, Inc. (the system and elution conditions were the same as those described above). FIG. 5-2 shows the elution pattern of the linear alpha-1,4-glucan under the same elution conditions.

The earliest eluted, detectable peak shown in FIG. 5-1 is designated as A, and the following peaks are designated as B, C, D - - - L. The peaks G through L were fractionated and purified.

(2) Analysis of the acid hydrolyzed material

Figure 6:
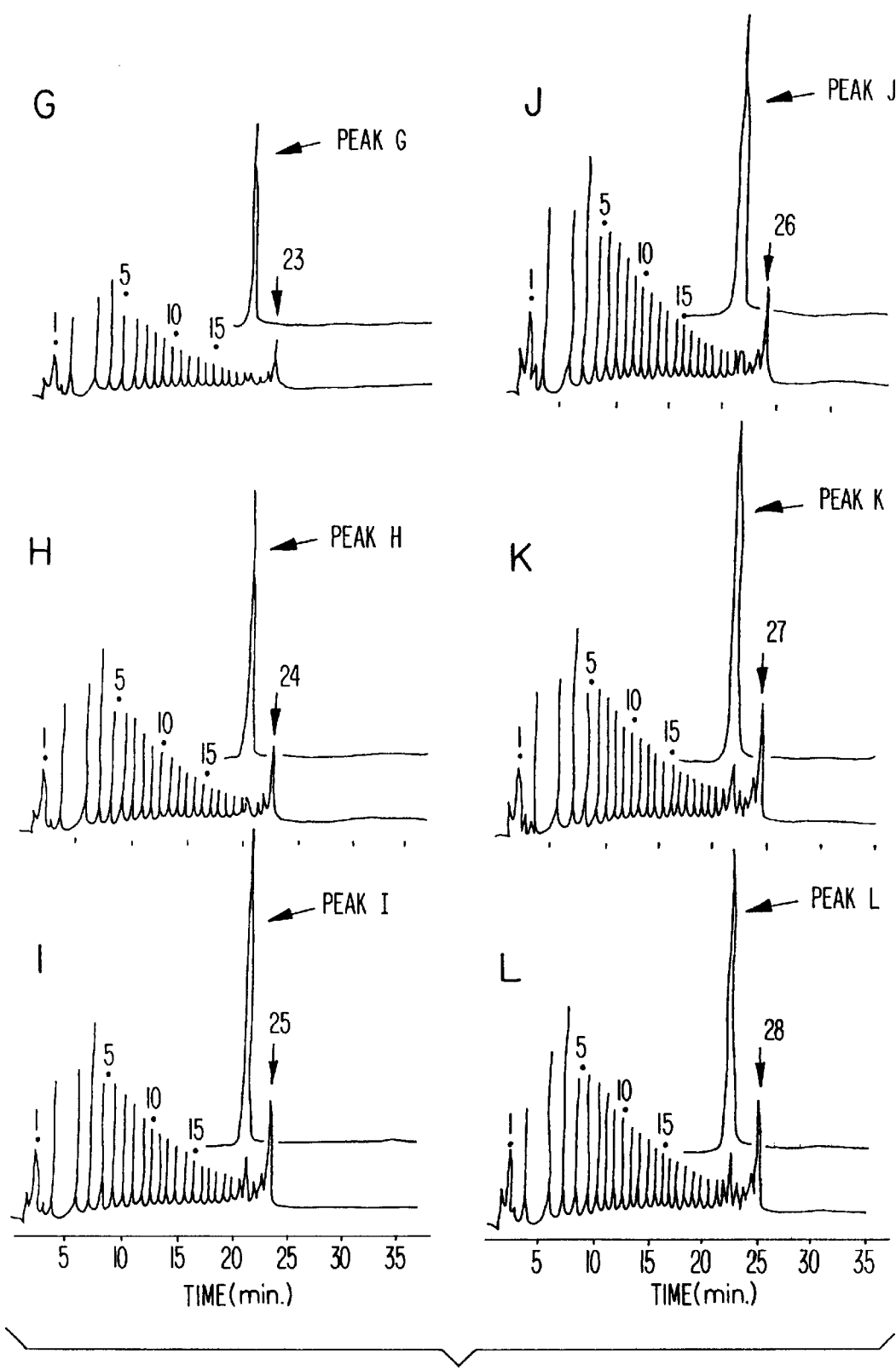
FIG. 6 shows elution patterns of intact and partially hydrolyzed cyclic glucan molecules which correspond to peak G-L in FIG. 5. The numbers in each peak indicate the DP.

The fractionated peaks G through L were hydrolyzed with a 0.1N HCl at 100° C. for 30 minutes. This condition is a condition resulting in partial hydrolysis. The hydrolyzed material was analyzed by the carbohydrate analysis system of DIONEX, Inc. (the system and elution conditions were the same as in Example 4). FIG. 6 shows the results.

The fraction of the above-described peak G was partially hydrolyzed with the acid, and degraded into glucose and a linear alpha-1,4-glucan having a DP of 2 to 23.

The intact peak G is eluted around the position of the linear alpha-1,4-glucan having a DP of 20. An interesting phenomenon was found in that the degraded material was eluted at a position for higher DP than the intact material. This phenomenon was also found in the other peaks, H through L, which suggested that the peaks G through L correspond to a cyclic glucan having only alpha-1,4-glucosidic bonds.

It is thought that the DP of the largest linear alpha-1,4-glucan which was produced in the aforementioned partial hydrolysis experiment corresponds to the DP of the cyclic glucan having only alpha-1,4-glucosidic bonds in each peak. Therefore, it was found that the DP of the peaks, G, H, I, J, K and L were 23, 24, 25, 26, 27 and 28, respectively. Also, it is estimated from the results that the DP of the peak A, which corresponds to the cyclic glucan having the lowest DP and only alpha-1,4-glucosidic bonds is 17.

On the other hand, the DP of the cyclic glucans having a much higher DP and only alpha-1,4-glucosidic bonds can be analyzed by gel filtration chromatography. The powder of the cyclic glucan having only alpha-1,4-glucosidic bonds obtained in each reaction time in Example 4 was dissolved in 250 μl of distilled water, and loaded onto a connected column of Superose 6 ((φ) 1 cm×30 cm, Pharmacia, Inc.) and Superdex 30 ((φ) 1 cm×30 cm, Pharmacia, Inc.), and eluted with a 150 mM sodium acetate solution.

Figure 7:
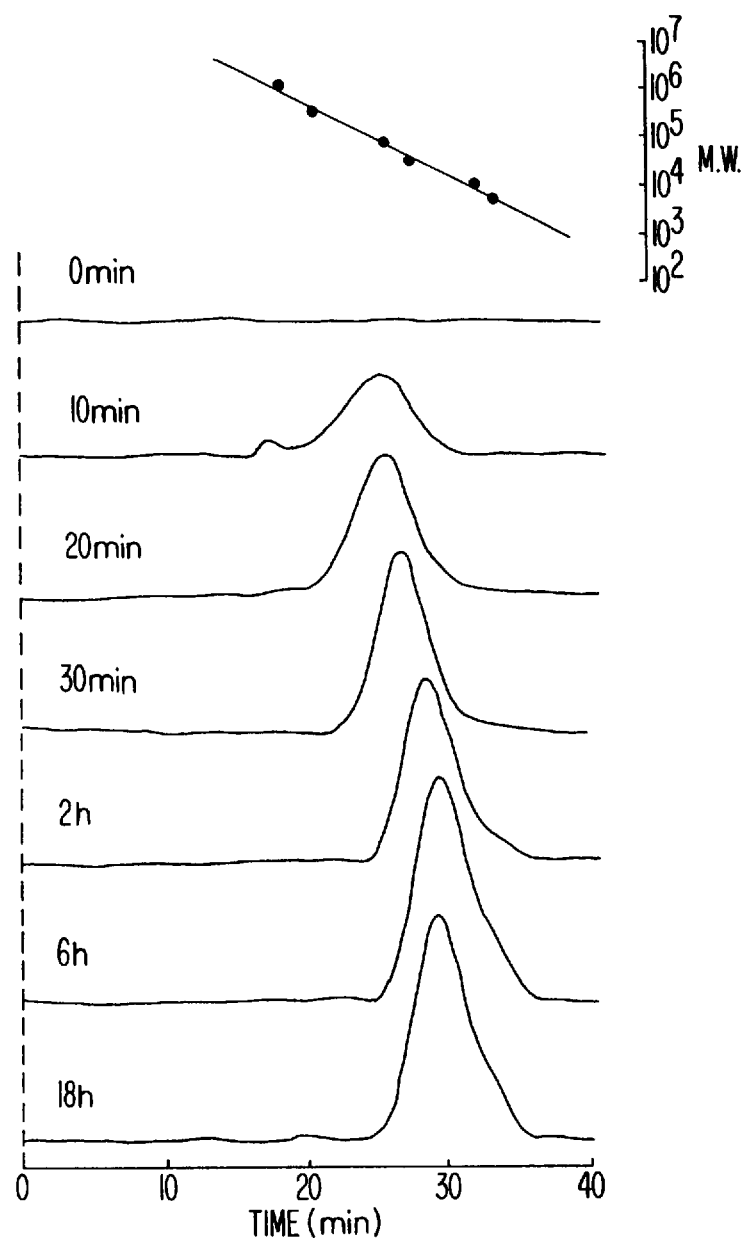
FIG. 7 shows elution patterns on gel filtration chromatography of a cyclic glucan having only alpha-1,4-glucosidic bonds obtained in Example 4.

As shown in FIG. 7, the cyclic glucan having only alpha-1,4-glucosidic bonds produced in the sample in which the reaction time of the D-enzyme was 10 minutes had an average molecular weight of about 70,000. As the reaction time of the D-enzyme increased, the molecular weight of the cyclic glucan having only alpha-1,4-glucosidic bonds was decreased. However, the average molecular weight of the cyclic glucan was unchanged at a level of about 15000 on and after the reaction time of 6 hours, and no further reduction of the molecular weight occurred. The molecular weight of the cyclic glucan was estimated using the synthetic amylose as a standard.

Thus, it is found that the DP of the cyclic glucan having only alpha-1,4-glucosidic bonds produced with the D-enzyme can arbitrarily be controlled in the range of from 17 to about several hundreds by changing the DP of the amylose which is used as a substrate, the amount of the D-enzyme, the reaction time, and the like.

Example 7

Preparation of the glucan of this invention

After dispersing 40 mg of the commercially available waxy corn starch in 2 ml of DMSO (dimethylsulfoxide), 18 ml of a 20 mM citric acid buffer (pH 7.0) containing 680 units of the D-enzyme purified in Example 1 were added to the starch solution, and reacted at 30° C. for 40 hours.

The reaction mixture was heated at 100° C. for 10 hours, and centrifuged to remove the denatured enzyme protein. To the supernatant, a 10-fold volume of ethanol was added to precipitate a glucan. Then, the resulting precipitate was freeze-dried to obtain about 40 mg of the powder of the glucans of this invention. The powder was a mixture of the glucan of this invention having only alpha-1,4-glucosidic bonds, the glucan of this invention having at least one alpha-1,6-glucosidic bond, and the glucan of this invention having a cyclic structure comprising only alpha-1,4-glucosidic bonds and an acyclic structure.

Example 8

Figure 8:
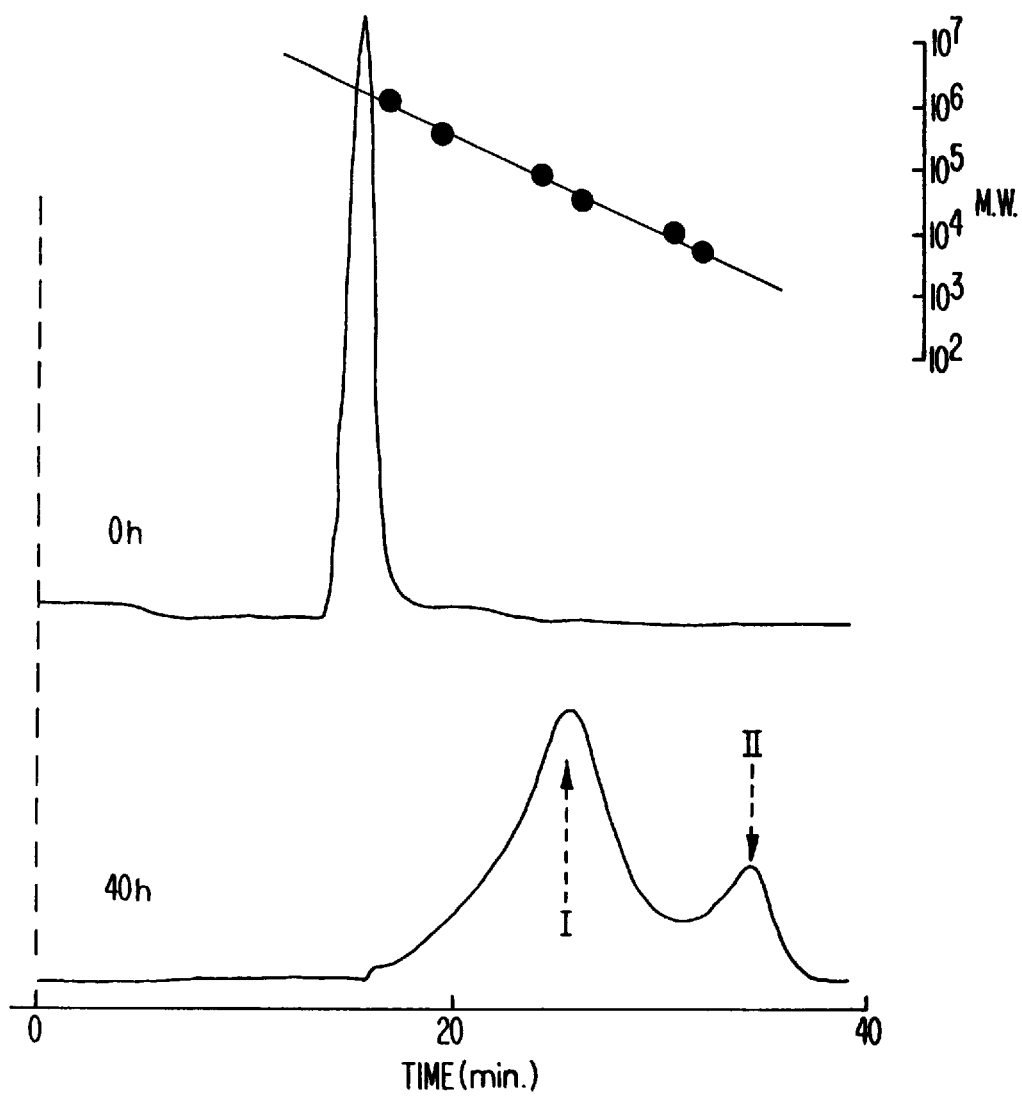
FIG. 8 shows elution patterns on gel filtration chromatography of the waxy corn starches before and after D-enzyme treatment.

Preparation of the glucan having at least one alpha-1,6-glucosidic bond in a cyclic structure and an acyclic structure of this invention The precipitate obtained in Example 7 was fractionated by gel filtration chromatography. The precipitate was dissolved in 250 μl of distilled water, and loaded onto a connected column of Superose 6 ((φ) 1 cm×30 cm, Pharmacia, Inc.) and Superdex 30 ((φ) 1 cm×30 cm, Pharmacia, Inc.), and eluted with a 150 mM sodium acetate solution. As shown in FIG. 8, the molecular weight of the amylopectin which was eluted in the void volume, was lowered by the reaction with the D-enzyme to produce two types of components which constitute Peak I having an average molecular weight of about 30,000 and Peak II having an average molecular weight of about 3,000. Peak II which had an average molecular weight of about 3,000 consisted essentially of cyclic glucans having only alpha-1,4-glucosidic bonds. On the other hand, Peak I which had an average molecular weight of about 30,000 consisted of a glucan having at least one alpha-1,6-glucosidic bond. Peak I was fractionated, and a glucan having at least one alpha-1,6-glucosidic bond was precipitated with the addition of a 10-fold volume of ethanol. The precipitate was centrifuged, recovered, and thereafter freeze-dried to obtain 20 mg of the glucan having at least one alpha-1,6-glucosidic bond. The molecular weight of the cyclic glucan was estimated using synthetic amylose as a standard.

Example 9
Preparation of the cyclic glucan having only alpha-1,4-glucosidic bonds After dissolving 20 mg of maltohexaose and 200 mg of glucose i-phosphate in 10 ml of a 100 mM citric acid buffer (pH 7.0) containing 5 mM adenosine monophosphate, 20 units of the D-enzyme prepared in Example 1, and 1 mg of the phosphorylase a (Sigma, Inc.) were added to the solution, and reacted at 30° C. for 2 hours.

After centrifuging the reaction solution, the supernatant was treated at 100° C. for 5 minutes, and centrifuged again to remove the denatured enzyme protein. To the supernatant, 50 units of glucoamylase were added to remove linear alpha-1,4-glucan, and then 10-fold volumes of ethanol was added to the solution to precipitate a cyclic glucan. The precipitate contained about 30 mg of a cyclic glucan having only alpha-1,4-glucosidic bonds. Moreover, the glucose 1-phosphate present in the precipitate was removed by gel filtration chromatography.

Figure 9:
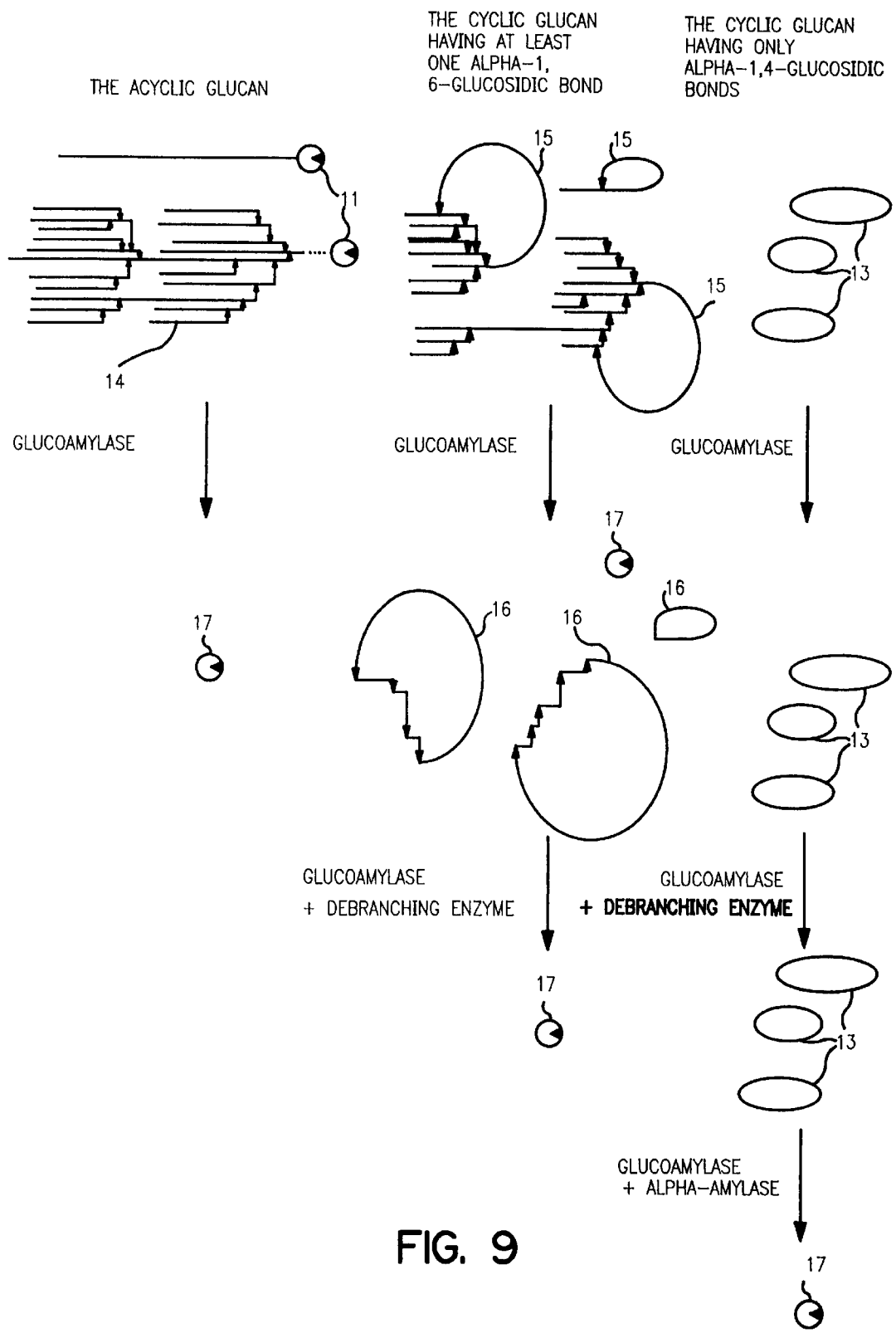
FIG. 9 is a scheme showing the steps of determining the acyclic structure, the cyclic structure having at least one alpha-1,6-glucosidic bonds, and the cyclic structure having only alpha-1,4-glucosidic bonds of the glucan obtained in Example 8.

Example 10
Confirmation that the material of Example 8 contains a cyclic structure including at least one alpha-1,6-glucosidic bond Glucoamylase is an enzyme capable of hydrolyzing successively the alpha-1,4-glucosidic bonds from the non-reducing end of a glucan such as starch. It is known that the enzyme also hydrolyzes the alpha-1,6-glucosidic bond from the non-reducing end, although the hydrolysis speed is slow. As shown in FIG. 9, amylose and amylopectin, which do not have a cyclic structure are degraded completely to the glucose (17) by the glucoamylase. However, in case of glucans having in their molecule a cyclic structure (13 and 15), only portions of the acyclic structure of the glucans are degraded by glucoamylase, and their cyclic structures (16) remain as a material which is not subject to the degradation by glucoamylase (hereinafter referred to as a glucoamylase resistant component). Moreover, the glucoamylase resistant component is classified into the cyclic glucan (16) having at least one alpha-1,6-glucosidic bond and the cyclic glucan (13) having only alpha-1,4-glucosidic bonds, according to their sensitivities to a starch debranching enzyme. That is, the glucoamylase resistant component which is not degraded by combined use of the debranching enzyme and glucoamylase, is considered to be the cyclic glucan (13) having only an alpha-1,4-glucosidic bonds. On the other hand, the glucoamylase resistant component, which is degraded by a combined use of the debranching enzyme and glucoamylase, is considered to be the cyclic glucan (16) having at least one alpha-1,6-glucosidic bond. However, the cyclic glucan (13) having only alpha-1,4-glucosidic bond which is not degraded by the combined use of the debranching enzyme and glucoamylase is degraded completely to glucose by a combined use of an endo-type alpha-amylase and glucoamylase. The use of these properties makes it possible to quantitate the amount of acyclic structure, the cyclic structure having at least one alpha-1,6-glucosidic bond, and the cyclic structure having only alpha-1,4-glucosidic bonds in the glucan samples.

The cyclic structures of the glucan obtained in Example 8 and amylopectin were quantitated using this method. Table 1 shows the results of the quantitation of the cyclic structures in the glucan obtained in Example 8 and amylopectin.

TABLE 1

|  | waxy corn starch (%) | material of example 8 (%) |
|---|---|---|
| portion of acyclic structure | 100.0 | 87.2 |
| portion of cyclic structure comprising only α-1, 4-glucoside bonds | 0.0 | 0.1 |
| portion of cyclic structure containing α-1, 6-glucoside bond | 0.0 | 12.7 |

After dissolving 10 mg of the material obtained in Example 8 or 10 mg of the amylopectin in 1 ml of DMSO, the solution was immediately diluted with 8 ml of a 100 mM sodium acetate buffer. Aliquots (900 μl) of the diluted solution were incubated for 4 h at 40° C. with 100 μl of (1) distilled water, (2) a glucoamylase solution (3) a solution containing debranching enzyme and glucoamylase, or (4) a solution containing endo-type alpha-amylase and glucoamylase. After the reaction was terminated, the glucose produced was measured by a commercially available glucose quantitation kit. The percentages of the acyclic structure, the cyclic structure having at least one alpha-1,6-glucosidic bond, and the cyclic structure having only alpha-1,4-glucosidic bonds in the glucan samples were determined according to the following calculation formulae.

$$\text{Acyclic structure (\%)} = \frac{x - c}{z - c} \times 100 \qquad \text{Formula 1}$$

$$\text{Cyclic structure having at least one alpha-1,6-glucosidic bond} = \frac{y - x}{z - c} \times 100 \qquad \text{Formula 2}$$

$$\text{Cyclic structure having only alpha-1,4-glucosidic bonds} = \frac{z - y}{z - c} \times 100 \qquad \text{Formula 3}$$

wherein c, x, y and z represent the amount of glucose produced in the reaction solution of (1), (2), (3) and (4), respectively. It can be seen from the results that the material obtained in Example 8 contains a glucan having a cyclic structure including at least one alpha-1,6-glucosidic bond.

Example 11
Measurement of the DP of the cyclic structure in the material of Example 8

After dissolving 10 mg of the material obtained in Example 8 in 1 ml of DMSO, 1 ml of 1M sodium acetate buffer (pH 5.5), 8 ml of distilled water, and 200 units of glucoamylase were added to the solution, and reacted at 40° C. for 1 hour. The reaction product was heated at 100° C. for 10 minutes, and thereafter centrifuged to remove the denatured enzyme. To the supernatant, a 10-fold volume of ethanol was added to precipitate a polysaccharide which was thereafter dried. The resulting polysaccharide was dissolved in 1 ml of distilled water. To the solution, 50 units of glucoamylase were added, and reacted at 40° C. for 1 hour. The reaction solution was heated at 100° C. for 10 minutes, and then centrifuged to remove the denatured enzyme. To the supernatant, a 10-fold volume of ethanol was added, and the precipitate thus produced was dried to obtain 1.1 mg of the powder of a glucoamylase resistant component (the cyclic structure).

The glucoamylase resistant component obtained as described above was dissolved in distilled water so that the concentration was 0.4% (w/v), and thereafter analyzed using the carbohydrate analysis system of DIONEX, Inc. (pump system: DX300, detector: PAD-2, column: CarboPacPA100). The elution procedure was conducted under the conditions of, for example, flow rate: 1 ml/min., NaOH concentration: 150 mM, sodium acetate concentration: 50 mM at 0 minute, 50 mM at 2 minutes, 350 mM at 37 minutes (Gradient curve No.3), 850 mM at 45 minutes (Gradient curve No.7), and 850 mM at 47 minutes.

As markers for comparing the DP, the linear alpha-1,4-glucan, and the glucan having only alpha-1,4-glucosidic bonds which was obtained in Example 2 were analyzed under the same conditions.

Figure 10:
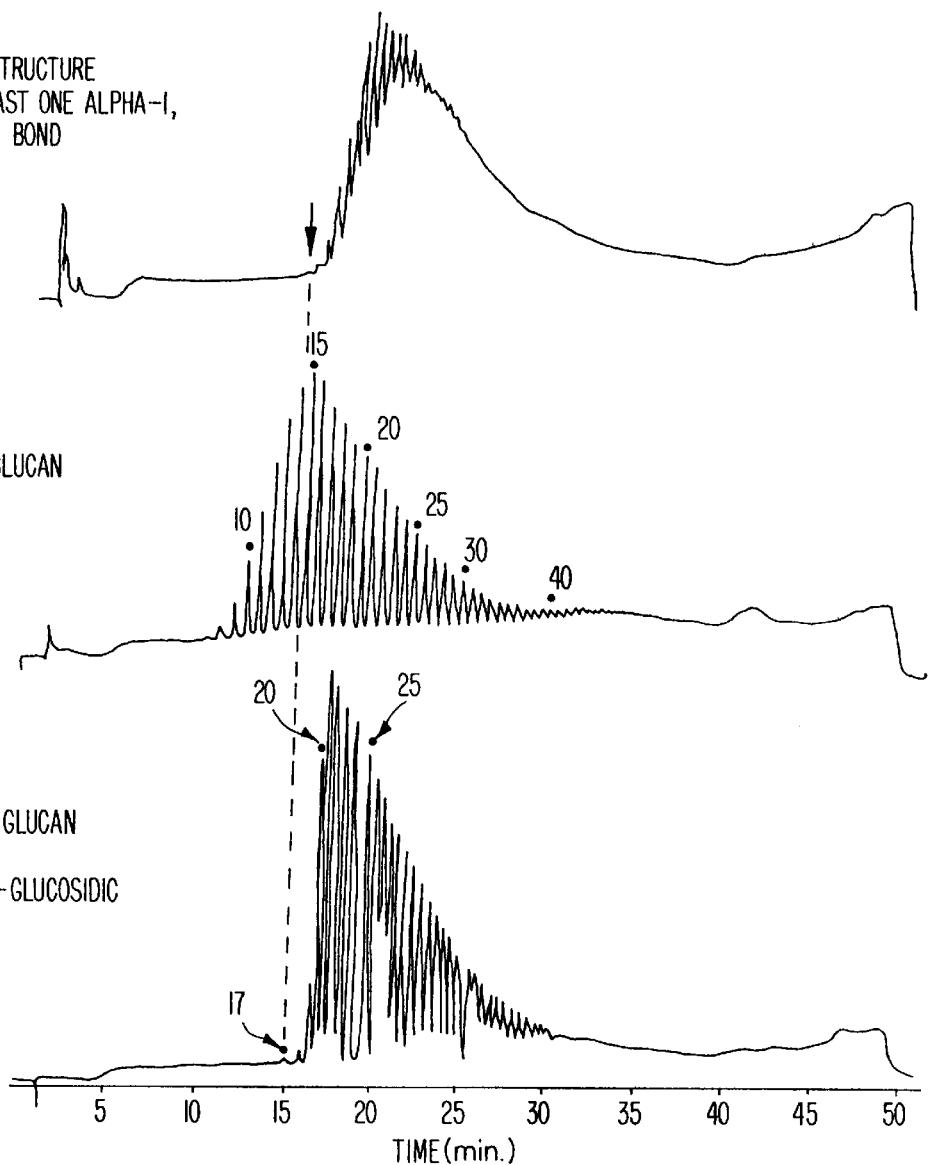
FIG. 10 shows elution patterns of the cyclic structure of the glucan having at least one alpha-1,6-glucosidic bonds obtained in Example 8, the linear alpha-1,4-glucan, and the cyclic glucan having only alpha-1,4-glucosidii bonds obtained in Example 2. The numbers in each pe indicate the DP.

As shown in FIG. 10, the resulting glucoamylase resistant component did not provide a clearly separated pattern which was obtained in the linear alpha-1,4-glucan, and the glucan having only alpha-1,4-glucosidic bonds. This result suggests that the glucoamylase resistant component contains various numbersof the alpha-1,6-glucosidic bonds. However, in view of the facts that the smallest peak (arrow) corresponds to the position indicating a DP of 15, and that the glucan having a cyclic structure is eluted earlier than the linear glucan having the same DP as described in Example 6, the DP of the smallest cyclic structure having at least one alpha-1,6-bond is considered to be at least 15.

Example 12
Solubility of the glucans of this invention

Each of the glucans obtained in Examples 6 and 8, and amylose, the waxy corn starch and the soluble starch (Wako Pure Chemicals, Inc.) as controls were individually suspended in distilled water so that the concentration was 10% (w/v), stirred vigorously by the vortex mixer, and thereafter centrifuged. The concentration of the saccharide dissolved at 0° C., 30° C., 60° C. and 100° C. in each supernatant was measured. Table 2 shows the results.

TABLE 2

|  | 0° C. | 30° C. | 60° C. | 100° C. |
| --- | --- | --- | --- | --- |
| cyclic glucan containing only α-1, 4-glucoside bonds (a material of example 2) | 9.98 (mg/ml) | 9.98 | 10.01 | 9.99 |
| portion of cyclic structure comprising only α-1, 4-glucoside bonds (a material of example 8) | 9.99 | 9.98 | 10.00 | 9.98 |
| amylose | 1.17 | 2.08 | 3.74 | 10.01 |
| waxy corn starch | 5.83 | 6.15 | 7.89 | 9.98 |
| soluble starch | 0.78 | 0.95 | 2.72 | 10.01 |

Table 2 shows that the glucans of the examples have a significantly higher solubility than the conventional starches.

Example 13
Retrogradation test of the glucan of this invention

Two hundred milligrams of each of the glucans obtained in Examples 2 and 8, and amylose, the waxy corn starch and the soluble starch (Wako Pure Chemicals, Inc.) as controls were individually placed into screw vials, to which 10 ml of water was added, and thereafter boiled and dissolved. After allowing these four samples to stand at 4° C. for 0 hour, 3 hours, 6 hours and 20 hours, 1 ml of each sample was transferred to a centrifuging tube, and centrifuged to measure the concentration of the saccharide dissolved in the supernatant. Table 3 shows the results.

TABLE 3

|  | 0hr | 3hr | 6hr | 20hr |
| --- | --- | --- | --- | --- |
| cyclic glucan containing only α-1, 4-glucoside bonds (a material of example 2) | 100 | 100.1 | 99.8 | 99.9 |

TABLE 3-continued

|  | 0hr | 3hr | 6hr | 20hr |
| --- | --- | --- | --- | --- |
| portion of cyclic structure comprising only α-1, 4-glucoside bonds (a material of example 8) | 100 | 100 | 100.1 | 99.8 |
| amylose | 100 | 85.6 | 72.4 | 58.2 |
| waxy corn starch | 100 | 97.2 | 94.5 | 88.3 |
| soluble starch | 100 | 96.8 | 80.2 | 70.3 |

Table 3 shows that the glucans of the examples exhibit significantly less retrogradation than the conventional starches.

Figure 11:
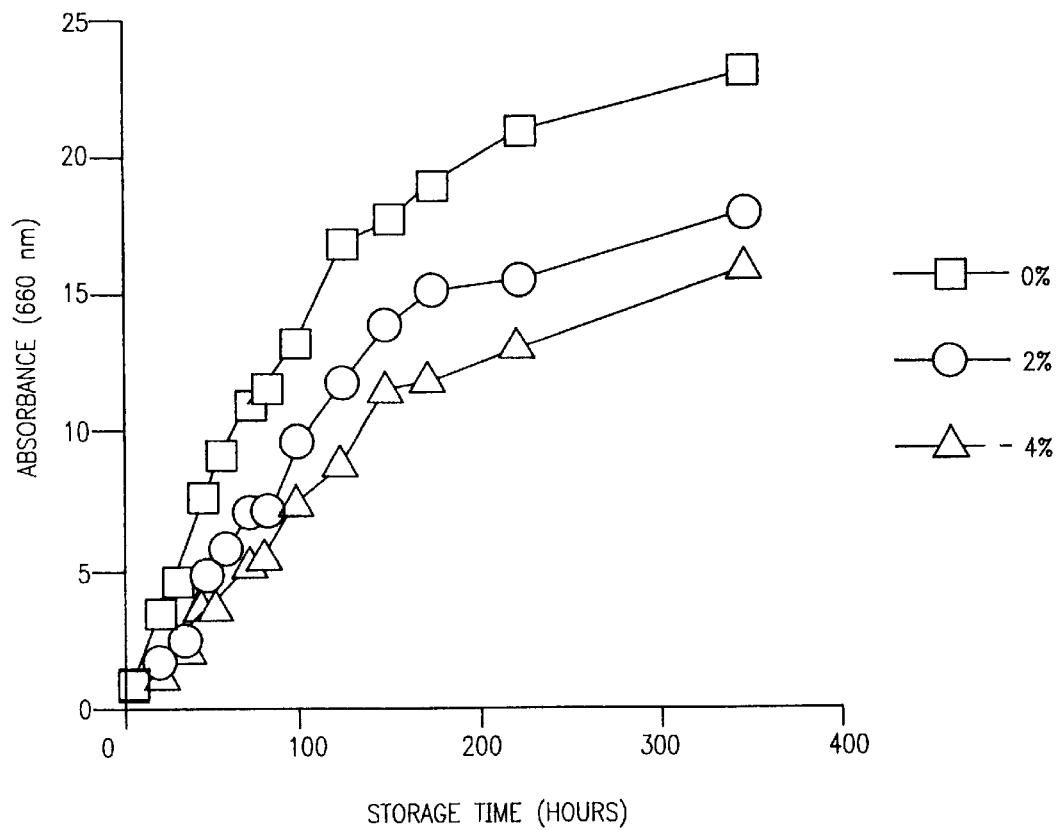
FIG. 11 shows the anti-retrograding effect on starch of the glucan obtained in Example 8.

Example 14
Anti-retrogradation effect of the glucan of this invention on a starch When a 4% (w/v) soluble starch solution which is completely gelatinized by heating is stored at 4° C., the soluble starch is quickly retrograded to become a cloudy paste solution. By using this phenomenon, the glucans of this invention were examined to test their anti-retrogradation effect. The glucan obtained in Example 8 was added to a 4% (w/v) soluble starch solution so that a final concentration of 0% (w/v), 2% (w/v), or 4% (w/v) was obtained, and stored at 4° C. Samples were taken at several time points, and cloudiness measured at a wavelength of 660 nm. FIG. 11 shows the results.

FIG. 11 shows that the glucan of Example 14 has an anti-retrogradation effect on starch.

Example 15
Viscosity of the glucans of this invention

After placing 1.6 g of each of the glucans obtained in Example 8, and the conventional waxy corn starch, soluble starch (Wako Pure Chemicals, Inc.) and Pinedex #1 (Matsutani Chemical, Inc.) as controls individually into vials and dispersing it with 8 ml of distilled water, 72 ml of dimethylsulfoxide were added to the dispersion, and the glucans were dissolved completely by stirring at room temperature. The viscosity of each solution was measured by the digital viscometer, DVL-B (Tokyo Keiki, Inc.; rotor; No.1, rotation frequency; 60 rpm, measurement time; 10 seconds). The viscosity of a solution of 72 ml of dimethylsulfoxide added to 8 ml of distilled water (90% DMS0 solution) was also measured as a control. The Pinedex #1 used herein is a starch which is more strongly hydrolyzed with alpha-amylase than the above-described soluble starch. Table 4 shows the results.

TABLE 4

|  | viscosity (mpa · s) |
| --- | --- |
| 90% DMSO solution | 5.3 |
| glucan obtained in example 8 | 6.4 |
| Pinedex #1 | 5.8 |
| soluble starch | 5.6 |
| waxy corn starch | 100.3 |

Table 4 shows that the paste solution of the example has a significantly lower viscosity than that of conventional waxy corn starch.

Example 16
Reactivity of the glucans of this invention

After dissolving 20 mg of each of the glucans obtained in Examples 2 and 8, and soluble starch (Wako Junyaku, Inc.) and Pinedex #1 (Matsutani Chemical, Inc.) as controls individually in 1 ml of distilled water, the reducing power of each solution is measured, according to the di-nitro salicylic acid method (by Sakuzo Fukui, Seibutsu Kagaku Jikkenho 1, Determination of Reduction and the like, Gakkai Shuppan Center). Table 5 shows the results.

TABLE 5

|  | amount of reduced sugar (mg/ml) |
| --- | --- |
| glucans obtained in example 2 and 8 | not detected (<0.01) |
| Pinedex #1 | 5.10 |
| soluble starch | 2.84 |

Table 5 shows that the glucans of the examples have a significantly lower reactivity than conventional starches.

Example 17

Phosphorylation of the glucans of this invention

Eight milligrams of each of the glucans obtained in Examples 2 and 8 were suspended in 1 ml of dimethylformamide, and reacted with 46 mg of phosphorus oxychloride. To the reaction solution, 9 ml of acetone were added to obtain 8 mg of each of the phosphorized glucans.

Example 18

Inclusion property (1) of the glucan of this invention

Figure 12:
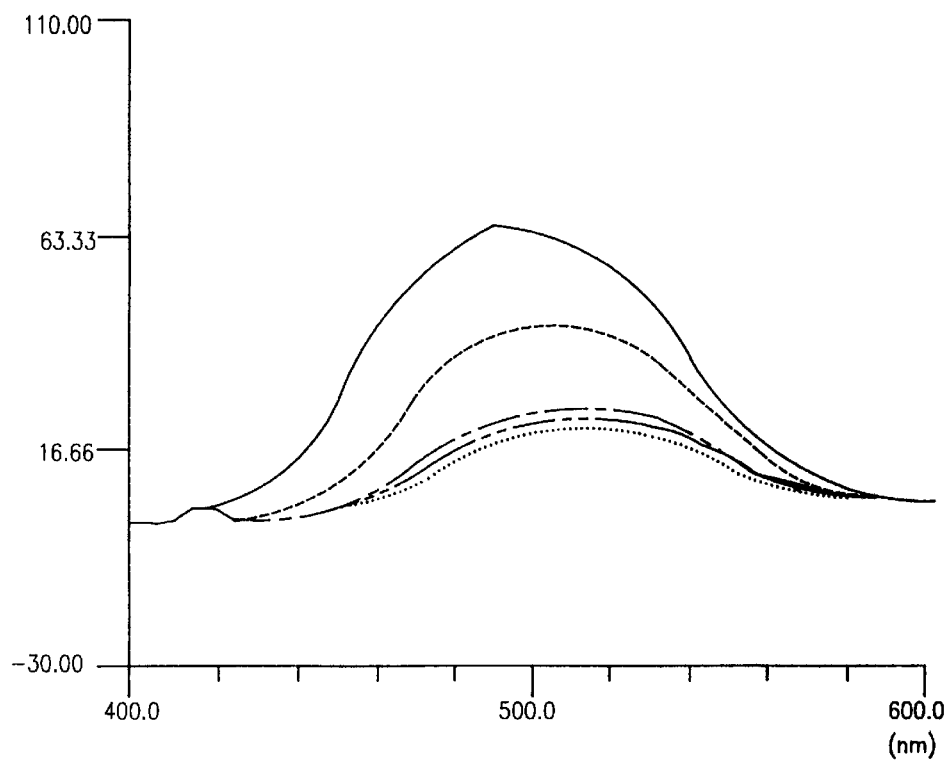
FIG. 12 shows the fluorescent spectrum of ANS in the presence of the cyclic glucan having only alpha-1,4-glucosidic bonds obtained in Example 2 (solid line), alpha-cyclodextrin (dashed line), pullulan (alternate long and short dash line), dextran (alternate long and two short dashes line), or a control (dotted line). The horizontal and vertical axis indicate the wavelength (nm) and spectrum strength, respectively.

It is known that 8-anilino-1-naphthalene sulfonic acid (ANS) shows an extremely weak fluorescence in an aqueous solution, however, it shows a strong fluorescence when included in the cavity of a cyclodextrin. In order to confirm whether the glucans of this invention include ANS to increase its fluorescence or not, 20 mg of each of the cyclic glucan having only alpha-1,4-glucosidic bonds which was obtained in Example 2, alpha-cyclodextrin, pullulan, and dextran were individually dissolved in 1 ml of 100 mM phosphate buffer. After adding 400 μM aqueous solution of ANS to the glucan solution and it was mixed well, the fluorescence spectrum of the solution was measured using a fluorescence spectrophotometer. As shown in FIG. 12, the fluorescence strength of the ANS in the presence of pullulan or dextran, which have no inclusion property, was not increased, while the fluorescence strength of ANS in the presence of alpha-cyclodextrin, which has an inclusion property, was increased. The fluorescence strength of the ANS in the presence of the glucan obtained in Example 2 was increased more than that of alpha-cyclodextrin, which indicates that the glucans of this invention have an inclusion property for ANS.

Example 19

Inclusion properties (2) of the glucan of this invention

Each of the cyclic glucans having only alpha-1,4-glucosidic bonds which were obtained in Example 2, commercially available amylose, and soluble starch were individually dissolved in distilled water so that the concentration was 2%(w/v). Then, one-tenth volumes of higher alcohol (1-octanol, etc.) or higher fatty acid (oleic acid, etc.) was added to the solution and vigorously mixed. The appearance of the solution was visually evaluated as follows. Table 6 shows the results. In table 6, (○) indicates that a large amount of the precipitate was formed, (Δ) indicates that a small amount of the precipitate was formed, and (×) indicates that no precipitate was formed.

TABLE 6

|  | 1-octanol | oleic acid |
| --- | --- | --- |
| cyclic glucan containing only α-1, 4-glucoside bonds | ○ | ○ |
| amylose | Δ | Δ |
| soluble starch | X | X |

As shown in Table 6, a large amount of the white precipitate was produced from the cyclic glucan having only alpha-1,4-glucosidic bonds which were obtained in Example 2, which indicates that the glucans of this invention have inclusion properties.

Example 20

Sports drinks containing the glucans of this invention

A sports drink using the glucan of this invention was prepared by blending the following components at proportions described in Table 7.

TABLE 7

| sodium chloride | 0.3 |
| --- | --- |
| vitamin C | 0.02 |
| sodium vitamin B$_1$ | 0.02 |
| magnesium chloride | 0.2 |
| calcium lactate | 0.2 |
| citric acid | 2.0 |
| sodium citrate | 1.5 |
| glucose | 50 |
| water | 1000 |
| cyclic glucan of example 2 | 100 |

The resulting sports drink had excellent digestive properties, and high energy exchange efficiency.

Example 21

Inclusion complex of glucan of this invention and linoleic acid.

To 100 parts of the cyclic glucan having only alpha-1,4-glucosidic bonds which was obtained in Example 2, 900 parts of water were added, stirred and dissolved. To the solution, 100 parts of linoleic acid were added, and stirred well. After stirring, the white precipitate fraction thus produced was freeze-dried to obtain the powder of the inclusion complex containing the glucan of this invention and linoleic acid.

Example 22

Inclusion complex of the glucan of this invention and menthol.

To 100 parts of the cyclic glucan having only alpha-1,4-glucosidic bonds which was obtained in Example 2, 900 parts of water were added, stirred and dissolved.

The solution was heated, to which 100 parts of the previously dissolved menthol were added, and stirred well. After stirring, the white precipitate fraction thus produced was freeze-dried to obtain the powder of the inclusion complex containing the glucan of this invention and menthol.

Example 23

A d hesive compositions containing the glucan of this invention

To 40 parts of the glucan having at least one alpha-1,6-glucosidic bond of Example 8, 60 parts of water were added, heated and dissolved. The solution exhibits excellent adhesive properties.

Example 24

Preparation of the cyclic glucan having only alpha-1,4-glucosidic bonds of this invention One gram of the enzyme immobilizing carrier, Kitopearli BCW-3503 (Fuji Boseki, Inc.) which was washed with distilled water, and 130 units (5 ml) of the purified D-enzyme solution containing a 20 mM Tris-buffer (pH 7.0) were incubated as stirring slowly at room temperature for 2 hours to adsorb the D-enzyme into the carrier. The reaction solution was filtered. When the D-enzyme activity of the filtrate was measured, little D-enzyme activity was detected. Therefore, it is thought that a major portion of the D-enzyme was immobilized to the carrier. To the D-enzyme immobilized carrier, 10 ml of 0.5% synthetic synthesized amylose (AS-30) solution are added, and reacted at pH 7 at 30° C. for 24 hours. The reaction solution was centrifuged, and the supernatant was treated at 100° C. for 5 minutes, and centrifuged again. After adding 10 units of glucoamylase to the supernatant and reacting it at 50° C. for 3 hours, a 10-fold volume of ethanol is added to the reaction solution to precipitate a cyclic glucan. The precipitate was freeze-dried to obtain 30 mg of a glucan powder. According to the same procedure as in Example 5, it was identified that the cyclic glucan having only alpha-1,4-glucosidic bonds was obtained.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A process for manufacturing a glucan selected from the group consisting of:

(a) a glucan composed of one cyclic structure containing at least fourteen alpha-1,4-glucosidic bonds;

(b) a glucan composed of one cyclic structure containing at least fourteen alpha-1,4-glucosidic bonds and an acyclic structure;

(c) a glucan composed of one cyclic structure containing at least fourteen alpha-1,4-glucosidic bonds and at least one alpha-1,6-glucosidic bond; and (d) a glucan composed of one cyclic structure containing at least fourteen alpha-1,4-glucosidic bonds and at least one alpha-1,6-glucosidic bond and an acyclic structure, wherein the process comprises reacting a linear alpha-1,4-glucan or a saccharide containing the linear alpha-1,4-glucan with a D-enzyme.

2. The process of claim 1, wherein said process is conducted in the presence of phosphorylase and glucose 1-phosphate.

3. The process of claim 1, wherein said process is conducted in the presence of an enzyme capable of cleaving an alpha-1,6-glucosidic bond.

4. The process of claim 1, wherein said linear alpha-1,4-glucan or saccharide is selected from the group consisting of malto-oligo saccharides, amylose, amylopectin, glycogen, starches, waxy starches, high amylose starches, soluble starches, dextrins, debranched starches, partially hydrolyzed starches, and enzyme synthesized starches with phosphorylase.

5. The process of claim 1, wherein the D-enzyme is immobilized.

6. A process for manufacturing a derivative of glucan selected from the group consisting of:

(a) a glucan composed of one cyclic structure containing at least fourteen alpha-1,4-glucosidic bonds;

(b) a glucan composed of one cyclic structure containing at least fourteen alpha-1,4-glucosidic bonds and an acyclic structure;

(c) a glucan composed of one cyclic structure containing at least fourteen alpha-1,4-glucosidic bonds and at least one alpha-1,6-glucosidic bond; and (d) a glucan composed of one cyclic structure containing at least fourteen alpha-1,4-glucosidic bonds and at least one alpha-1,6-glucosidic bond and an acyclic structure, wherein the process comprises reacting a linear alpha-1,4-glucan or a saccharide containing the linear alpha-1,4-glucan with a D-enzyme, and modifying said glucan by a derivatization selected from the group consisting of etherification, esterification, crosslinking, and grafting.

7. A process for manufacturing a derivative of glucan selected from the groups consisting of:

(a) a glucan composed of one cyclic structure containing at least fourteen alpha-1,4-glucosidic bonds;

(b) a glucan composed of one cyclic structure containing at least fourteen alpha-1,4-glucosidic bonds and an acyclic structure;

(c) a glucan composed of one cyclic structure containing at least fourteen alpha-1,4-glucosidic bonds and at least one alpha-1,6-glucosidic bond; and (d) a glucan composed of one cyclic structure containing at least fourteen alpha-1,4-glucosidic bonds and at least one alpha-1,6-glucosidic bond and an acyclic structure, wherein the process comprises reacting a derivative of linear alpha-1,4-glucan or a saccharide containing the linear alpha-1,4-glucan which is modified by a derivatization selected from the group consisting of etherification, esterification, crosslinking, and grafting, with a D-enzyme.

8. The process of claim 7, wherein said derivative of linear alpha-1,4-glucan or saccharide is selected from the group consisting of derivatives of malto-oligo saccharides, amylose, amylopectin, glycogen, starches, waxy starches, high amylose starches, soluble starches, dextrins, debranched starches, partially hydrolyzed starches, and enzyme synthesized starches with phosphorylase.

\* \* \* \* \*